(12) United States Patent
Van Lue et al.

(10) Patent No.: US 9,173,698 B2
(45) Date of Patent: Nov. 3, 2015

(54) ELECTROSURGICAL TISSUE SEALING AUGMENTED WITH A SEAL-ENHANCING COMPOSITION

(75) Inventors: Stephen Van Lue, Winter Springs, FL (US); Joseph Charles Eder, Woodside, CA (US); Miriam H. Taimisto, San Jose, CA (US)

(73) Assignee: Aesculap AG, Tuttlingen (DE)

( * ) Notice: Subject to any disclaimer, the term of this patent is extended or adjusted under 35 U.S.C. 154(b) by 1025 days.

(21) Appl. No.: 13/110,848

(22) Filed: May 18, 2011

(65) Prior Publication Data

US 2012/0071871 A1    Mar. 22, 2012

Related U.S. Application Data

(60) Provisional application No. 61/384,201, filed on Sep. 17, 2010.

(51) Int. Cl.
*A61B 18/18* (2006.01)
*A61B 18/14* (2006.01)
*A61B 18/00* (2006.01)

(52) U.S. Cl.
CPC ..... *A61B 18/1445* (2013.01); *A61B 2018/0063* (2013.01); *A61B 2018/1455* (2013.01)

(58) Field of Classification Search
CPC ............. A61B 2018/0063; A61B 2018/00607; A61B 2018/1455; A61B 18/1442
USPC ................... 606/49, 51, 52, 213–216
See application file for complete search history.

(56) References Cited

U.S. PATENT DOCUMENTS

| 3,356,408 A | 12/1967 | Stutz |
| 3,527,224 A | 9/1970 | Rabinowitz |
| 3,709,215 A | 1/1973 | Richmond |

(Continued)

FOREIGN PATENT DOCUMENTS

| CA | 2061215 A1 | 8/1992 |
| EP | 0440385 A2 | 8/1991 |

(Continued)

OTHER PUBLICATIONS

International Search Report for International Application No. PCT/US2011/046593 dated Mar. 14, 2012.

(Continued)

*Primary Examiner* — Joseph Stoklosa
*Assistant Examiner* — Jocelyn D Ram
(74) *Attorney, Agent, or Firm* — RatnerPrestia

(57) ABSTRACT

Embodiments of the disclosed technology provide systems, devices, and methods of creating an electrosurgical tissue seal that is augmented with a seal-enhancing composition. One embodiment of a device includes a set of opposing electrosurgical jaws configured to be able to close on a targeted tissue-sealing site; the jaws have a reservoir configured to hold a tissue seal-enhancing composition. The reservoir is in communication with a surface of the tissue-sealing site when the jaws are closed on the site, and the electrosurgical device is configured to deliver the tissue seal-enhancing composition to the site during an electrosurgical procedure. The device is further configured to deliver sufficient radiofrequency energy to the site such that the targeted tissue and the tissue seal-enhancing composition at the tissue-sealing site are processed to form a high integrity sealed tissue site.

28 Claims, 11 Drawing Sheets

(56) References Cited

U.S. PATENT DOCUMENTS

| | | |
|---|---|---|
| 3,742,955 A | 7/1973 | Battista et al. |
| 3,845,771 A | 11/1974 | Vise |
| 3,920,021 A | 11/1975 | Hiltebrandt |
| 3,970,088 A | 7/1976 | Morrison |
| 4,018,230 A | 4/1977 | Ochiai et al. |
| 4,041,952 A | 8/1977 | Morrison, Jr. et al. |
| 4,072,153 A | 2/1978 | Swartz |
| 4,094,320 A | 6/1978 | Newton et al. |
| 4,231,372 A | 11/1980 | Newton |
| 4,492,231 A | 1/1985 | Auth |
| 4,532,924 A | 8/1985 | Auth et al. |
| 4,590,934 A | 5/1986 | Malis et al. |
| 4,671,274 A | 6/1987 | Sorochenko |
| 4,972,846 A | 11/1990 | Owens et al. |
| 4,976,717 A | 12/1990 | Boyle |
| 4,979,948 A | 12/1990 | Geddes et al. |
| 4,998,527 A | 3/1991 | Meyer |
| 5,037,379 A | 8/1991 | Clayman et al. |
| 5,041,101 A | 8/1991 | Seder et al. |
| 5,059,782 A | 10/1991 | Fukuyama |
| 5,078,736 A | 1/1992 | Behl |
| 5,108,408 A | 4/1992 | Lally |
| 5,133,713 A | 7/1992 | Huang et al. |
| 5,151,102 A | 9/1992 | Kamiyama et al. |
| 5,156,613 A | 10/1992 | Sawyer |
| 5,178,618 A | 1/1993 | Kandarpa |
| 5,190,541 A | 3/1993 | Abele et al. |
| 5,207,691 A | 5/1993 | Nardella |
| 5,217,030 A | 6/1993 | Yoon |
| 5,234,425 A | 8/1993 | Fogarty et al. |
| 5,250,074 A | 10/1993 | Wilk et al. |
| 5,267,998 A | 12/1993 | Hagen |
| 5,269,780 A | 12/1993 | Roos |
| 5,269,782 A | 12/1993 | Sutter |
| 5,273,524 A | 12/1993 | Fox et al. |
| 5,277,201 A | 1/1994 | Stern |
| 5,281,216 A | 1/1994 | Klicek |
| 5,282,799 A | 2/1994 | Rydell |
| 5,290,287 A | 3/1994 | Boebel et al. |
| 5,295,990 A | 3/1994 | Levin |
| 5,300,068 A | 4/1994 | Rosar et al. |
| 5,300,087 A | 4/1994 | Knoepfler |
| 5,312,023 A | 5/1994 | Green et al. |
| 5,324,289 A | 6/1994 | Eggers |
| 5,330,471 A | 7/1994 | Eggers |
| 5,330,502 A | 7/1994 | Hassler et al. |
| 5,336,229 A | 8/1994 | Noda |
| 5,336,237 A | 8/1994 | Chin et al. |
| 5,341,807 A | 8/1994 | Nardella |
| 5,342,381 A | 8/1994 | Tidemand |
| 5,352,223 A | 10/1994 | McBrayer et al. |
| 5,352,235 A | 10/1994 | Koros et al. |
| 5,354,336 A | 10/1994 | Kelman et al. |
| 5,356,408 A | 10/1994 | Rydell |
| 5,374,277 A | 12/1994 | Hassler |
| 5,377,415 A | 1/1995 | Gibson |
| 5,383,899 A * | 1/1995 | Hammerslag ............ 606/214 |
| 5,391,166 A | 2/1995 | Eggers |
| 5,395,369 A | 3/1995 | McBrayer et al. |
| 5,396,900 A | 3/1995 | Slater et al. |
| 5,397,320 A | 3/1995 | Essig et al. |
| 5,403,312 A | 4/1995 | Yates et al. |
| 5,417,687 A | 5/1995 | Nardella et al. |
| 5,423,814 A | 6/1995 | Zhu et al. |
| 5,431,676 A | 7/1995 | Dubrul et al. |
| 5,438,302 A | 8/1995 | Goble |
| 5,443,463 A | 8/1995 | Stern et al. |
| 5,443,470 A | 8/1995 | Stern et al. |
| 5,445,638 A | 8/1995 | Rydell et al. |
| 5,447,513 A | 9/1995 | Davison et al. |
| 5,449,355 A | 9/1995 | Rhum et al. |
| 5,456,684 A | 10/1995 | Schmidt et al. |
| 5,458,598 A | 10/1995 | Feinberg et al. |
| 5,462,546 A | 10/1995 | Rydell |
| 5,472,442 A | 12/1995 | Klicek |
| 5,480,399 A | 1/1996 | Hebborn |
| 5,482,054 A | 1/1996 | Slater et al. |
| 5,484,435 A | 1/1996 | Fleenor et al. |
| 5,484,436 A | 1/1996 | Eggers et al. |
| 5,496,312 A | 3/1996 | Klicek |
| 5,496,317 A | 3/1996 | Goble et al. |
| 5,514,134 A | 5/1996 | Rydell et al. |
| 5,520,698 A | 5/1996 | Koh |
| 5,531,744 A | 7/1996 | Nardella et al. |
| 5,540,684 A | 7/1996 | Hassler, Jr. |
| 5,540,685 A | 7/1996 | Parins et al. |
| 5,542,945 A | 8/1996 | Fritzsch |
| 5,549,637 A | 8/1996 | Crainich |
| 5,556,397 A | 9/1996 | Long et al. |
| 5,558,100 A | 9/1996 | Cox |
| 5,558,671 A | 9/1996 | Yates |
| 5,562,700 A | 10/1996 | Huitema et al. |
| 5,562,701 A | 10/1996 | Huitema et al. |
| 5,562,702 A | 10/1996 | Huitema et al. |
| 5,562,720 A | 10/1996 | Stern et al. |
| 5,569,243 A | 10/1996 | Kortenbach et al. |
| 5,571,100 A | 11/1996 | Goble et al. |
| 5,573,535 A | 11/1996 | Viklund |
| 5,578,052 A | 11/1996 | Koros et al. |
| 5,599,350 A | 2/1997 | Schulze et al. |
| 5,601,224 A | 2/1997 | Bishop et al. |
| 5,603,700 A | 2/1997 | Daneshvar |
| 5,603,711 A | 2/1997 | Parins et al. |
| 5,611,803 A | 3/1997 | Heaven et al. |
| 5,624,452 A | 4/1997 | Yates |
| 5,637,110 A | 6/1997 | Pennybacker et al. |
| 5,637,111 A | 6/1997 | Sutcu et al. |
| 5,653,692 A | 8/1997 | Masterson et al. |
| 5,658,281 A | 8/1997 | Heard |
| 5,662,662 A | 9/1997 | Bishop et al. |
| 5,662,676 A | 9/1997 | Koninckx |
| 5,665,085 A | 9/1997 | Nardella |
| 5,665,100 A | 9/1997 | Yoon |
| 5,667,526 A | 9/1997 | Levin |
| 5,669,907 A | 9/1997 | Platt, Jr. et al. |
| 5,673,840 A | 10/1997 | Schulze et al. |
| 5,673,841 A | 10/1997 | Schulze et al. |
| 5,674,184 A | 10/1997 | Hassler, Jr. |
| 5,674,220 A | 10/1997 | Fox et al. |
| 5,675,184 A | 10/1997 | Matsubayashi et al. |
| 5,680,982 A | 10/1997 | Schulze et al. |
| 5,681,282 A | 10/1997 | Eggers et al. |
| 5,683,385 A | 11/1997 | Kortenbach et al. |
| 5,683,388 A | 11/1997 | Slater |
| 5,688,270 A | 11/1997 | Yates et al. |
| 5,690,675 A | 11/1997 | Sawyer et al. |
| 5,693,051 A | 12/1997 | Schulze et al. |
| 5,697,949 A | 12/1997 | Giurtino et al. |
| 5,700,261 A | 12/1997 | Brinkerhoff |
| 5,702,390 A | 12/1997 | Austin et al. |
| 5,704,534 A | 1/1998 | Huitema et al. |
| 5,707,369 A | 1/1998 | Vaitekunas et al. |
| 5,709,680 A | 1/1998 | Yates et al. |
| 5,713,896 A | 2/1998 | Nardella |
| 5,715,832 A | 2/1998 | Koblish et al. |
| 5,718,703 A | 2/1998 | Chin |
| 5,720,719 A | 2/1998 | Edwards et al. |
| 5,728,143 A | 3/1998 | Gough et al. |
| 5,733,283 A | 3/1998 | Malis et al. |
| 5,735,289 A | 4/1998 | Pfeffer et al. |
| 5,735,848 A | 4/1998 | Yates et al. |
| 5,735,849 A | 4/1998 | Baden et al. |
| 5,741,285 A | 4/1998 | McBrayer et al. |
| 5,746,750 A | 5/1998 | Prestel et al. |
| 5,749,895 A | 5/1998 | Sawyer et al. |
| 5,755,717 A | 5/1998 | Yates et al. |
| 5,776,130 A | 7/1998 | Buysse et al. |
| 5,788,662 A | 8/1998 | Antanavich et al. |
| 5,797,941 A | 8/1998 | Schulze et al. |
| 5,810,811 A | 9/1998 | Yates et al. |
| 5,817,091 A | 10/1998 | Nardella et al. |
| 5,817,092 A | 10/1998 | Behl |
| 5,823,066 A | 10/1998 | Huitema et al. |
| 5,833,689 A | 11/1998 | Long |

(56) References Cited

U.S. PATENT DOCUMENTS

| | | | |
|---|---|---|---|
| 5,836,990 A | 11/1998 | Li | |
| 5,840,077 A | 11/1998 | Rowden et al. | |
| 5,855,576 A | 1/1999 | LeVeen et al. | |
| 5,860,975 A | 1/1999 | Goble et al. | |
| 5,891,142 A | 4/1999 | Eggers et al. | |
| 5,893,835 A | 4/1999 | Witt et al. | |
| 5,893,874 A | 4/1999 | Bourque et al. | |
| 5,931,835 A | 8/1999 | Mackey | |
| 5,931,836 A | 8/1999 | Hatta et al. | |
| 5,954,720 A | 9/1999 | Wilson et al. | |
| 5,976,128 A | 11/1999 | Schilling et al. | |
| 5,979,453 A | 11/1999 | Savage et al. | |
| 6,003,517 A | 12/1999 | Sheffield et al. | |
| 6,004,319 A | 12/1999 | Goble et al. | |
| 6,030,384 A | 2/2000 | Nezhat | |
| 6,033,401 A * | 3/2000 | Edwards et al. | 606/41 |
| 6,050,993 A | 4/2000 | Tu et al. | |
| 6,050,995 A | 4/2000 | Durgin | |
| 6,056,744 A | 5/2000 | Edwards | |
| 6,059,766 A | 5/2000 | Greff | |
| 6,059,782 A | 5/2000 | Novak et al. | |
| 6,066,139 A | 5/2000 | Ryan et al. | |
| 6,068,626 A | 5/2000 | Harrington et al. | |
| 6,071,281 A | 6/2000 | Burnside et al. | |
| 6,074,386 A | 6/2000 | Goble et al. | |
| 6,086,586 A | 7/2000 | Hooven | |
| 6,090,106 A | 7/2000 | Goble et al. | |
| 6,093,186 A | 7/2000 | Goble | |
| 6,096,037 A | 8/2000 | Mulier et al. | |
| 6,099,550 A | 8/2000 | Yoon | |
| 6,123,701 A | 9/2000 | Nezhat | |
| H1904 H | 10/2000 | Yates et al. | |
| 6,142,992 A | 11/2000 | Cheng et al. | |
| 6,152,920 A | 11/2000 | Thompson et al. | |
| 6,152,932 A | 11/2000 | Ternstrom | |
| 6,162,220 A | 12/2000 | Nezhat | |
| 6,174,309 B1 | 1/2001 | Wrublewski et al. | |
| 6,179,832 B1 | 1/2001 | Jones et al. | |
| 6,203,541 B1 | 3/2001 | Keppel | |
| 6,203,542 B1 | 3/2001 | Ellsberry et al. | |
| 6,206,877 B1 | 3/2001 | Kese et al. | |
| 6,210,406 B1 | 4/2001 | Webster | |
| 6,212,426 B1 | 4/2001 | Swanson | |
| 6,217,894 B1 | 4/2001 | Sawhney et al. | |
| 6,228,084 B1 | 5/2001 | Kirwan, Jr. | |
| 6,234,178 B1 | 5/2001 | Goble et al. | |
| 6,241,139 B1 | 6/2001 | Milliman et al. | |
| 6,245,069 B1 | 6/2001 | Gminder | |
| 6,254,601 B1 | 7/2001 | Burbank et al. | |
| 6,258,085 B1 | 7/2001 | Eggleston | |
| 6,277,114 B1 | 8/2001 | Bullivant et al. | |
| 6,283,963 B1 | 9/2001 | Regula | |
| 6,287,304 B1 | 9/2001 | Eggers et al. | |
| 6,290,715 B1 | 9/2001 | Sharkey et al. | |
| 6,293,942 B1 | 9/2001 | Goble et al. | |
| 6,293,946 B1 | 9/2001 | Thorne | |
| 6,296,636 B1 | 10/2001 | Cheng et al. | |
| 6,312,430 B1 | 11/2001 | Wilson et al. | |
| 6,322,494 B1 | 11/2001 | Bullivant et al. | |
| 6,327,505 B1 | 12/2001 | Medhkour et al. | |
| 6,334,861 B1 | 1/2002 | Chandler et al. | |
| 6,350,274 B1 | 2/2002 | Li | |
| 6,361,559 B1 | 3/2002 | Houser et al. | |
| 6,364,879 B1 | 4/2002 | Chen et al. | |
| 6,371,956 B1 | 4/2002 | Wilson et al. | |
| 6,391,024 B1 | 5/2002 | Sun et al. | |
| 6,391,029 B1 | 5/2002 | Hooven et al. | |
| 6,391,048 B1 * | 5/2002 | Ginn et al. | 606/213 |
| 6,398,779 B1 | 6/2002 | Buysse et al. | |
| 6,398,781 B1 | 6/2002 | Goble et al. | |
| H2037 H | 7/2002 | Yates et al. | |
| 6,416,509 B1 | 7/2002 | Goble et al. | |
| 6,428,550 B1 | 8/2002 | Vargas et al. | |
| 6,436,096 B1 | 8/2002 | Hareyama | |
| 6,464,702 B2 | 10/2002 | Schulze et al. | |
| 6,485,486 B1 | 11/2002 | Trembly et al. | |
| 6,485,489 B2 | 11/2002 | Teirstein et al. | |
| 6,491,690 B1 | 12/2002 | Goble et al. | |
| 6,494,881 B1 | 12/2002 | Bales et al. | |
| 6,500,176 B1 | 12/2002 | Truckai et al. | |
| 6,514,252 B2 | 2/2003 | Nezhat et al. | |
| 6,517,530 B1 | 2/2003 | Kleven | |
| 6,520,185 B1 | 2/2003 | Bommannan et al. | |
| 6,533,784 B2 | 3/2003 | Truckai et al. | |
| 6,546,933 B1 | 4/2003 | Yoon | |
| 6,554,829 B2 | 4/2003 | Schulze et al. | |
| 6,564,806 B1 | 5/2003 | Fogarty et al. | |
| 6,565,560 B1 | 5/2003 | Goble et al. | |
| 6,565,561 B1 | 5/2003 | Goble et al. | |
| 6,584,360 B2 | 6/2003 | Francischelli et al. | |
| 6,610,074 B2 | 8/2003 | Santilli | |
| 6,616,654 B2 | 9/2003 | Mollenauer | |
| 6,616,659 B1 | 9/2003 | de la Torre et al. | |
| 6,619,529 B2 | 9/2003 | Green et al. | |
| 6,622,731 B2 * | 9/2003 | Daniel et al. | 128/898 |
| 6,623,482 B2 | 9/2003 | Pendekanti et al. | |
| 6,626,901 B1 | 9/2003 | Treat et al. | |
| 6,645,198 B1 | 11/2003 | Bommannan et al. | |
| 6,645,201 B1 | 11/2003 | Utley et al. | |
| 6,648,839 B2 | 11/2003 | Manna et al. | |
| 6,652,518 B2 | 11/2003 | Wellman et al. | |
| 6,656,177 B2 | 12/2003 | Truckai et al. | |
| 6,666,859 B1 | 12/2003 | Fleenor et al. | |
| 6,673,085 B1 | 1/2004 | Berg | |
| 6,676,660 B2 | 1/2004 | Wampler et al. | |
| 6,682,526 B1 | 1/2004 | Jones et al. | |
| 6,682,527 B2 | 1/2004 | Strul | |
| 6,695,840 B2 | 2/2004 | Schulze | |
| 6,699,245 B2 | 3/2004 | Dinger et al. | |
| 6,719,754 B2 | 4/2004 | Underwood et al. | |
| 6,722,371 B1 | 4/2004 | Fogarty et al. | |
| 6,723,092 B2 * | 4/2004 | Brown et al. | 606/41 |
| 6,736,814 B2 | 5/2004 | Manna et al. | |
| 6,743,229 B2 | 6/2004 | Buysse et al. | |
| 6,746,488 B1 | 6/2004 | Bales | |
| 6,752,154 B2 | 6/2004 | Fogarty et al. | |
| 6,752,803 B2 | 6/2004 | Goldman et al. | |
| 6,770,070 B1 | 8/2004 | Balbierz | |
| 6,770,072 B1 | 8/2004 | Truckai et al. | |
| 6,808,525 B2 | 10/2004 | Latterell et al. | |
| 6,817,974 B2 | 11/2004 | Cooper et al. | |
| 6,821,273 B2 | 11/2004 | Mollenauer | |
| 6,837,888 B2 | 1/2005 | Ciarrocca et al. | |
| 6,840,938 B1 | 1/2005 | Morley et al. | |
| 6,843,789 B2 | 1/2005 | Goble | |
| 6,852,108 B2 | 2/2005 | Barry et al. | |
| 6,889,089 B2 | 5/2005 | Behl et al. | |
| 6,893,435 B2 | 5/2005 | Goble | |
| 6,896,672 B1 | 5/2005 | Eggers et al. | |
| 6,896,673 B2 | 5/2005 | Hooven | |
| 6,905,506 B2 | 6/2005 | Burbank et al. | |
| 6,913,579 B2 | 7/2005 | Truckai et al. | |
| 6,918,907 B2 | 7/2005 | Kelly et al. | |
| 6,918,909 B2 | 7/2005 | Ohyama et al. | |
| 6,923,803 B2 | 8/2005 | Goble | |
| 6,926,712 B2 | 8/2005 | Phan | |
| 6,929,642 B2 | 8/2005 | Xiao et al. | |
| 6,936,048 B2 | 8/2005 | Hurst | |
| 6,939,346 B2 | 9/2005 | Kannenberg et al. | |
| 6,953,461 B2 | 10/2005 | McClurken et al. | |
| 6,981,628 B2 | 1/2006 | Wales | |
| 7,033,356 B2 | 4/2006 | Latterell et al. | |
| 7,063,699 B2 | 6/2006 | Hess et al. | |
| 7,090,637 B2 | 8/2006 | Danitz et al. | |
| 7,090,673 B2 | 8/2006 | Dycus et al. | |
| 7,090,685 B2 | 8/2006 | Kortenbach et al. | |
| 7,094,235 B2 | 8/2006 | Francischelli | |
| 7,101,371 B2 | 9/2006 | Dycus et al. | |
| 7,101,372 B2 | 9/2006 | Dycus et al. | |
| 7,101,373 B2 | 9/2006 | Dycus et al. | |
| 7,118,587 B2 | 10/2006 | Dycus et al. | |
| 7,125,409 B2 | 10/2006 | Truckai et al. | |
| 7,137,980 B2 | 11/2006 | Buysse et al. | |
| 7,159,750 B2 | 1/2007 | Racenet et al. | |

(56) References Cited

U.S. PATENT DOCUMENTS

| | | |
|---|---|---|
| 7,166,102 B2 | 1/2007 | Fleenor et al. |
| 7,169,146 B2 | 1/2007 | Truckai et al. |
| 7,179,254 B2 | 2/2007 | Pendekanti et al. |
| 7,195,627 B2 | 3/2007 | Amoah et al. |
| 7,220,260 B2 | 5/2007 | Fleming et al. |
| 7,238,195 B2 | 7/2007 | Viola |
| 7,250,048 B2 | 7/2007 | Francischelli et al. |
| 7,267,677 B2 | 9/2007 | Johnson et al. |
| 7,270,664 B2 | 9/2007 | Johnson et al. |
| 7,276,068 B2 | 10/2007 | Johnson et al. |
| 7,278,991 B2 | 10/2007 | Morris et al. |
| 7,291,143 B2 | 11/2007 | Swanson |
| 7,364,577 B2 | 4/2008 | Wham et al. |
| 7,367,972 B2 | 5/2008 | Francischelli et al. |
| 7,410,483 B2 | 8/2008 | Danitz et al. |
| 7,494,039 B2 | 2/2009 | Racenet et al. |
| 7,506,790 B2 | 3/2009 | Shelton, IV et al. |
| 7,517,356 B2 | 4/2009 | Heinrich |
| 7,540,872 B2 | 6/2009 | Schechter et al. |
| 7,549,564 B2 | 6/2009 | Boudreaux |
| 7,571,845 B2 * | 8/2009 | Viola ............... 227/180.1 |
| 7,588,565 B2 | 9/2009 | Marchitto et al. |
| 7,624,902 B2 | 12/2009 | Marczyk et al. |
| 7,641,651 B2 | 1/2010 | Nezhat et al. |
| 7,655,007 B2 * | 2/2010 | Baily ............... 606/51 |
| 7,703,653 B2 | 4/2010 | Shah et al. |
| 7,794,461 B2 | 9/2010 | Eder et al. |
| 7,798,385 B2 | 9/2010 | Boyden et al. |
| 7,803,156 B2 | 9/2010 | Eder et al. |
| 7,862,565 B2 | 1/2011 | Eder et al. |
| 7,942,874 B2 | 5/2011 | Eder et al. |
| 8,827,995 B2 * | 9/2014 | Schaller et al. ............ 606/51 |
| 2001/0029367 A1 | 10/2001 | Fleenor et al. |
| 2002/0062123 A1 | 5/2002 | McClurken et al. |
| 2002/0062136 A1 | 5/2002 | Hillstead et al. |
| 2002/0107514 A1 | 8/2002 | Hooven |
| 2002/0124853 A1 | 9/2002 | Burbank et al. |
| 2002/0128643 A1 | 9/2002 | Simpson et al. |
| 2002/0133193 A1 * | 9/2002 | Ginn et al. ............... 606/216 |
| 2002/0151882 A1 | 10/2002 | Marko et al. |
| 2002/0165541 A1 * | 11/2002 | Whitman ............... 606/48 |
| 2002/0177848 A1 | 11/2002 | Truckai et al. |
| 2002/0183738 A1 | 12/2002 | Chee et al. |
| 2003/0078577 A1 | 4/2003 | Truckai et al. |
| 2003/0144652 A1 | 7/2003 | Baker |
| 2003/0144653 A1 | 7/2003 | Francischelli et al. |
| 2003/0158547 A1 | 8/2003 | Phan |
| 2003/0171745 A1 | 9/2003 | Francischelli et al. |
| 2003/0216726 A1 | 11/2003 | Eggers et al. |
| 2003/0216733 A1 | 11/2003 | McClurken et al. |
| 2003/0229344 A1 | 12/2003 | Dycus et al. |
| 2003/0236549 A1 | 12/2003 | Bonadio et al. |
| 2004/0006339 A1 | 1/2004 | Underwood et al. |
| 2004/0010245 A1 | 1/2004 | Cerier et al. |
| 2004/0068274 A1 | 4/2004 | Hooven |
| 2004/0097919 A1 | 5/2004 | Wellman et al. |
| 2004/0122423 A1 | 6/2004 | Dycus et al. |
| 2004/0143263 A1 | 7/2004 | Schechter et al. |
| 2004/0199226 A1 | 10/2004 | Shadduck |
| 2004/0210282 A1 * | 10/2004 | Flock et al. ............ 607/96 |
| 2004/0236320 A1 | 11/2004 | Protsenko et al. |
| 2005/0010212 A1 | 1/2005 | McClurken et al. |
| 2005/0015085 A1 | 1/2005 | McClurken et al. |
| 2005/0021026 A1 | 1/2005 | Baily |
| 2005/0021027 A1 | 1/2005 | Shields et al. |
| 2005/0033276 A1 | 2/2005 | Adachi |
| 2005/0033277 A1 | 2/2005 | Clague et al. |
| 2005/0033278 A1 | 2/2005 | McClurken et al. |
| 2005/0070895 A1 | 3/2005 | Ryan et al. |
| 2005/0070978 A1 | 3/2005 | Bek et al. |
| 2005/0090819 A1 | 4/2005 | Goble |
| 2005/0096645 A1 | 5/2005 | Wellman et al. |
| 2005/0096694 A1 | 5/2005 | Lee |
| 2005/0107781 A1 | 5/2005 | Ostrovsky et al. |
| 2005/0107784 A1 | 5/2005 | Moses et al. |
| 2005/0113817 A1 | 5/2005 | Isaacson et al. |
| 2005/0113820 A1 | 5/2005 | Goble et al. |
| 2005/0119654 A1 | 6/2005 | Swanson et al. |
| 2005/0131390 A1 | 6/2005 | Heinrich et al. |
| 2005/0149073 A1 | 7/2005 | Arani et al. |
| 2005/0165444 A1 * | 7/2005 | Hart et al. ............... 606/213 |
| 2005/0171533 A1 | 8/2005 | Latterell et al. |
| 2005/0187561 A1 | 8/2005 | Lee-Sepsick et al. |
| 2005/0192633 A1 | 9/2005 | Montpetit |
| 2005/0196421 A1 | 9/2005 | Hunter et al. |
| 2005/0203500 A1 | 9/2005 | Saadat et al. |
| 2005/0203504 A1 | 9/2005 | Wham et al. |
| 2005/0209664 A1 | 9/2005 | Hunter et al. |
| 2005/0226682 A1 | 10/2005 | Chersky et al. |
| 2005/0256522 A1 | 11/2005 | Francischelli et al. |
| 2005/0256524 A1 | 11/2005 | Long et al. |
| 2005/0261676 A1 | 11/2005 | Hall et al. |
| 2006/0025765 A1 | 2/2006 | Landman et al. |
| 2006/0025812 A1 | 2/2006 | Shelton, IV |
| 2006/0041254 A1 | 2/2006 | Francischelli et al. |
| 2006/0052778 A1 | 3/2006 | Chapman et al. |
| 2006/0052779 A1 | 3/2006 | Hammill |
| 2006/0064084 A1 | 3/2006 | Haemmerich et al. |
| 2006/0079872 A1 | 4/2006 | Eggleston |
| 2006/0085031 A1 * | 4/2006 | Bettuchi ............... 606/215 |
| 2006/0167451 A1 | 7/2006 | Cropper |
| 2006/0190029 A1 | 8/2006 | Wales |
| 2006/0199999 A1 | 9/2006 | Ikeda et al. |
| 2006/0217709 A1 | 9/2006 | Couture et al. |
| 2006/0226196 A1 | 10/2006 | Hueil et al. |
| 2006/0229665 A1 | 10/2006 | Wales et al. |
| 2006/0253117 A1 | 11/2006 | Hovda et al. |
| 2006/0258954 A1 | 11/2006 | Timberlake et al. |
| 2006/0259035 A1 | 11/2006 | Nezhat et al. |
| 2006/0271037 A1 | 11/2006 | Maroney et al. |
| 2006/0271042 A1 | 11/2006 | Latterell et al. |
| 2006/0287674 A1 | 12/2006 | Ginn et al. |
| 2006/0289602 A1 | 12/2006 | Wales et al. |
| 2006/0293655 A1 | 12/2006 | Sartor |
| 2007/0005061 A1 | 1/2007 | Eder et al. |
| 2007/0049920 A1 | 3/2007 | McClurken et al. |
| 2007/0062017 A1 | 3/2007 | Dycus et al. |
| 2007/0073340 A1 | 3/2007 | Shelton, IV et al. |
| 2007/0123852 A1 | 5/2007 | Deem et al. |
| 2007/0128174 A1 | 6/2007 | Kleinsek et al. |
| 2007/0129726 A1 | 6/2007 | Eder et al. |
| 2007/0156140 A1 | 7/2007 | Baily |
| 2007/0173804 A1 | 7/2007 | Wham et al. |
| 2007/0173805 A1 | 7/2007 | Weinberg et al. |
| 2007/0173811 A1 | 7/2007 | Couture et al. |
| 2007/0179497 A1 | 8/2007 | Eggers et al. |
| 2007/0185482 A1 | 8/2007 | Eder et al. |
| 2007/0244538 A1 | 10/2007 | Eder et al. |
| 2007/0250113 A1 | 10/2007 | Hegeman et al. |
| 2007/0265613 A1 | 11/2007 | Edelstein et al. |
| 2007/0282318 A1 | 12/2007 | Spooner et al. |
| 2007/0282320 A1 | 12/2007 | Buysse et al. |
| 2008/0172052 A1 | 7/2008 | Eder et al. |
| 2008/0188844 A1 | 8/2008 | McGreevy et al. |
| 2008/0195093 A1 | 8/2008 | Couture et al. |
| 2008/0221565 A1 | 9/2008 | Eder et al. |
| 2008/0221616 A1 * | 9/2008 | Ginn et al. ............... 606/214 |
| 2008/0228179 A1 | 9/2008 | Eder et al. |
| 2008/0275446 A1 | 11/2008 | Messerly |
| 2008/0294222 A1 | 11/2008 | Schechter |
| 2008/0308607 A1 | 12/2008 | Timm et al. |
| 2009/0138006 A1 | 5/2009 | Bales et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0182323 A1 | 7/2009 | Eder et al. |
| 2009/0198272 A1 | 8/2009 | Kerver et al. |
| 2009/0209953 A1 | 8/2009 | Schoenman |
| 2009/0240245 A1 | 9/2009 | Deville et al. |
| 2009/0299367 A1 | 12/2009 | Ginnebaugh et al. |
| 2010/0042093 A9 | 2/2010 | Wham et al. |
| 2010/0049194 A1 * | 2/2010 | Hart et al. ............... 606/51 |
| 2010/0076427 A1 | 3/2010 | Heard |
| 2010/0094282 A1 | 4/2010 | Kabaya et al. |

(56) References Cited

U.S. PATENT DOCUMENTS

| | | |
|---|---|---|
| 2010/0100122 A1 | 4/2010 | Hinton |
| 2010/0280508 A1 | 11/2010 | Eder |
| 2010/0298823 A1 | 11/2010 | Cao et al. |
| 2011/0098700 A1* | 4/2011 | Tamai et al. .......... 606/41 |

FOREIGN PATENT DOCUMENTS

| | | |
|---|---|---|
| EP | 0487269 A1 | 5/1992 |
| EP | 0502268 A1 | 9/1992 |
| EP | 0562195 A1 | 9/1993 |
| EP | 0658333 A1 | 6/1995 |
| EP | 0923907 A1 | 6/1999 |
| EP | 0833593 B1 | 2/2001 |
| EP | 0737446 B1 | 12/2002 |
| EP | 0717960 B1 | 2/2003 |
| EP | 0869742 B1 | 5/2003 |
| EP | 0873089 B1 | 10/2003 |
| EP | 0742696 B1 | 11/2003 |
| EP | 1041933 B1 | 3/2004 |
| EP | 1004277 B1 | 7/2004 |
| EP | 0959786 B1 | 9/2004 |
| EP | 0913126 B1 | 10/2004 |
| EP | 0956827 B1 | 10/2004 |
| EP | 1472984 A1 | 11/2004 |
| EP | 1621146 A2 | 2/2006 |
| EP | 1645237 A1 | 4/2006 |
| EP | 0875209 B1 | 5/2006 |
| EP | 1293170 B1 | 6/2006 |
| EP | 1293169 B1 | 7/2006 |
| EP | 1064886 B1 | 8/2006 |
| EP | 1767164 A1 | 3/2007 |
| EP | 1518498 B1 | 12/2007 |
| EP | 1862138 A1 | 12/2007 |
| EP | 1039862 B1 | 5/2008 |
| EP | 1532933 B1 | 5/2008 |
| EP | 1707143 B1 | 6/2008 |
| EP | 1518499 B1 | 8/2008 |
| EP | 1632192 B1 | 3/2009 |
| EP | 1486177 B1 | 8/2009 |
| EP | 1852081 B1 | 8/2009 |
| EP | 1747761 B1 | 10/2009 |
| EP | 2106764 A2 | 10/2009 |
| EP | 2 174 612 | 4/2010 |
| JP | 2003088534 | 3/2003 |
| JP | 2004049566 | 2/2004 |
| JP | 2005144193 | 6/2005 |
| JP | 2008301955 | 12/2008 |
| WO | WO92/22257 A1 | 12/1992 |
| WO | WO93/08754 A1 | 5/1993 |
| WO | WO94/00060 A1 | 1/1994 |
| WO | WO94/26179 A1 | 11/1994 |
| WO | WO95/02371 A2 | 1/1995 |
| WO | WO96/05776 A1 | 2/1996 |
| WO | WO96/16605 A1 | 6/1996 |
| WO | WO96/23449 A1 | 8/1996 |
| WO | WO97/24073 A1 | 7/1997 |
| WO | WO97/24074 A1 | 7/1997 |
| WO | WO98/12999 A2 | 4/1998 |
| WO | WO98/43548 A1 | 10/1998 |
| WO | WO98/53750 A1 | 12/1998 |
| WO | WO99/23933 A2 | 5/1999 |
| WO | WO99/52459 A1 | 10/1999 |
| WO | WO99/56646 A1 | 11/1999 |
| WO | WO00/13192 A1 | 3/2000 |
| WO | WO00/13193 A1 | 3/2000 |
| WO | WO01/12090 A1 | 2/2001 |
| WO | WO01/35846 A1 | 5/2001 |
| WO | WO01/54602 A2 | 8/2001 |
| WO | WO01/58372 A1 | 8/2001 |
| WO | WO01/58373 A1 | 8/2001 |
| WO | WO01/82812 A1 | 11/2001 |
| WO | WO02/24092 A1 | 3/2002 |
| WO | WO02/058542 A2 | 8/2002 |
| WO | WO02/067798 A1 | 9/2002 |
| WO | WO03/088806 A2 | 10/2003 |
| WO | WO03/103522 A1 | 12/2003 |
| WO | WO2004/032596 A2 | 4/2004 |
| WO | WO2004/032776 A1 | 4/2004 |
| WO | WO2004/073490 A2 | 9/2004 |
| WO | WO2004/098383 A2 | 11/2004 |
| WO | WO2005/009213 A2 | 2/2005 |
| WO | WO2005/034729 A2 | 4/2005 |
| WO | WO2005/079901 A1 | 9/2005 |
| WO | WO2005/115251 A1 | 12/2005 |
| WO | WO2006/060431 A1 | 6/2006 |
| WO | WO2007/002227 A2 | 1/2007 |
| WO | WO2007/082061 A2 | 7/2007 |
| WO | WO2008/094554 A2 | 8/2008 |
| WO | WO2008/124112 A1 | 10/2008 |

OTHER PUBLICATIONS (Arthrocare); Arthrocare receives clearance to market coblation-based devices for gynecology and laparoscopic surgery: clearance includes plasma forceps and 21 specific indications; Business Wire; p. 524; Oct. 25, 2001.

(Business Wire); Radiofrequency energy proven effective against leading cause of obstructive sleep apnea; Business Wire; p09140175; Sep. 14, 1998.

(Curon); Curon announces the publication of data supporting durability and effectiveness of STRETTA® system—positive one year follow-up data of U.S. clinical trial published in gastrointestinal endoscopy; PR Newswire; pNYTH10307022002; Feb. 7, 2002.

(Curon); Curon medical announces presentation of positive clinical study results of STRETTA® procedure for gastroesophageal reflux disease (GERD); PR Newswire; pNYW07920032002; Mar. 20, 2002.

(Enable); Enable medical introduces second generation bipolar scissors; Health Industry Today; pNA; Dec. 1998.

(Everest) Everest medical announces introduction of 3mm bipolar forceps; PR Newswire; p1002MNW021; Oct. 2, 1996.

(Everest) Everest medical discusses patent status: forecasts $1 million revenue first quarter: introduces next generation bipolar scissors; PR Newswire; pN/A; Mar. 31, 1994.

(Everest) Everest medical introduces new QUADRIPOLAR} cutting forceps at the global congress for gynecologic endoscopy meeting; PR Newswire; p. 8927; Nov. 8, 1999.

(Everest) Everest medical reports record first quarter results: introduces next generation bipolar scissors; PR Newswire; pN/A; Apr. 19, 1994.

(Everest) Quadripolar cutting forceps introduced by Everest Medical; Health Industry Today; vol. 63; No. 1; pNA; Jan. 2000.

(Novare); U.S. patent issued for Novare Surgical Systems Cygnet® surgical clamp: Novare signs multi-year supply agreement with Boston Scientific; PR Newswire; pNA; Sep. 2, 2003.

Aoki et al.; Thoracoscopic resection of the lung with the ultrasonic scalpel; Ann thorac Surg; vol. 67; No. 4; pp. 1181-1183; Apr. 1999.

Bergamaschi et al.; Laparoscopic intracorporeal bowel resection with ultrasound versus electrosurgical dissection; JSLS; vol. 5; No. 1; pp. 17-20; Jan.-Mar. 2001.

Eichfeld et al.; Evaluation of ultracision in lung metastatic surgery; Ann Thorac Surg; vol. 70; No. 4; pp. 1181-1184; Oct. 2000.

ERBE Elektromedizin GmbH; ERBE BiClamp Brochure; http://www.erbe-med.com/erbe/media/Marketingmaterialien/85100-139_ERBE_EN_BiClamp_D024676.pdf; downloaded Jan. 24, 2011; 6 pgs.

GYRUS ACMI (an Olympus Company); PKS Seal (product page); http://www.gyrusacmi.com/user/display.cfm?display=product&pid=9024; downloaded Jan. 24, 2011; 1 page.

GYRUS Medical; Cutting Forceps (Product Information); downloaded Oct. 5, 2005.

GYRUS Medical; LP Scissors (Product Information); downloaded Oct. 5, 2005.

GYRUS Medical; Lyons} Dissecting Forceps (Product Information); downloaded Oct. 5, 2005.

GYRUS Medical; Micro/Macro-Jaw Forceps (Product Information); downloaded Oct. 5, 2005.

(56) References Cited

OTHER PUBLICATIONS

GYRUS Medical; Seal} Open Forceps (Product Information); downloaded Oct. 5, 2005.
Hayashi et al.; Experimental and clinical evaluation of the harmonic scalpel in thoracic surgery; Kurume Med J; vol. 46; No. 1; pp. 25-29; 1999.
Hefni et al.; Safety and efficacy of using the ligasure vessel sealing system for securing the pedicles in vaginal hysterectomy: randomized controlled trial; BJOG; vol. 112; No. 3; pp. 329-333; Mar. 2005.
Heniford et al.; Initial results with an electrothermal bipolar vessel sealer; Surg Endosc; vol. 15; No. 8; pp. 799-801; Aug. 2001.
Johnson & Johnson Gateway, LLC; The Gynecare Versapoint (Product Information); http://jnjgateway.com/home/jhtml?loc=USENG&page=view Content&id=edea000100001747 downloaded Oct. 20, 2005.
Kamat et al.; Superiority of electrocautery over the suture method for achieving cervical cone bed hemostasis; Obstet Gynecol; vol. 102; No. 4; pp. 726-730; Oct. 2003.
Kennedy et al.; High-burst-strength, feedback-controlled bipolar vessel sealing; Surg Endosc; vol. 12; No. 6; pp. 876-878; Jun. 1998.
Kim et al.; Design and fabrication of a locomotive mechanism for capsule-type endoscopes using shape memory alloys (SMAs); IEEE/ASME Trans on Mechatronics; vol. 10; No. 1; pp. 77-86; Feb. 2005.
Kovac; Transvaginal hysterectomy: rationale and surgical approach; Obstet. Gynecol.; vol. 103; pp. 1321-1325; 2004.
Landman et al.; Evaluation of a vessel sealing system, bipolar electrosurgery, harmonic scalpel, . . . in a porcine model; J. urol; vol. 169; No. 2; pp. 697-700; Feb. 2003.
Levy, et al.; Update on hysterectomy: new technology and techniques; A Supp. To OBG Maganagement; Feb. 2003.
Levy, et al.; Use of a new vessel ligation device during vaginal hysterectomy (presentation abstract); presented at FIGO 2000; Washington, D.C.; 2000.
Lin et al.; Application of ultrasonic scalpel in gynecologic operative laparoscopy; Chin Med J (Engl.); vol. 114; No. 12; pp. 1283-1285; Dec. 2001.
Live Tissue Connect Technologies; company profile; (http://www.onemedplace.com/database/compdisplay_print,php?CompanyID=11508); 1 pg.; Oct. 19, 2010 (downloaded Feb. 7, 2011).
Lyons et al.; An innovative bipolar instrument for laparoscopic surgery; JSLS; vol. 9; No. 1; pp. 39-41; Jan.-Mar. 2005.
McClurken et al.; Collagen shrinkage and vessel sealing; Technical brief #300. Dover, NH: Tissue Link Medical; 2001.
Nojarov et al.; High-energy scissors mode; Phys Rev C Nucl Phys; vol. 51; No. 5; pp. 2449-2456; 1995 (http://arxiv.org/abs/nucl-th/9502001v1).
Parikh et al.; Three dimensional virtual reality model of the normal female pelvic floor; Annals of Bimedical Engineering; vol. 32; pp. 292-296; Feb. 2004.
Refractec, Inc.; Medical use of radiofrequency (RF) energy; (http://www.locateadoc.com/Site_Tools/Print.cfm); 2 pgs.; Aug. 23, 2008 (downloaded Feb. 7, 2011).
Sages 2001 Hands-On Course I—Taking it the next level: advanced laparoscopic techniques; http://www.sages.org/01program/syllabi/ho1/ho1.html#schirme; 24 pgs.; downloaded Oct. 5, 2005.
SAGES 2001 Nurses Program, Session 1; http://sages.org/01program/syllabi/nurse/nurse.html; downloaded Jan. 24, 2011; 5 pgs.
Srisombut et al.; Laparoscopic hysterectomy using laparoscopic coagulating shears: experience of 15 cases; J. Med Assoc Thai; vol. 83; No. 8; pp. 915-920; Aug. 2000.
SURGRX 510(K) Summary (# K031133); Palo Alto, CA; 5 pgs.; Jul. 3, 2003.
TREAT; A new thermal device for sealing and dividing blood vessels; http://www.starioninstruments.com/PDFs/Treat.pdf; downloaded Jun. 29, 2005; 2 pgs.
Tyco Healthcare; The LigaSure Vessel Sealing System (Brochure); Apr. 2002; 8 pgs.
Valleylab Products; Valleylab Products—Electrosurgical Forceps: The surgeon's choice for quality and precision (product information); http://www.valleylab.com/product/es/accessories/forceps_over.html; downloaded Oct. 20, 2005.
Valleylab Products; Valleylab Products—Ligasure} vessel sealing system (product information); http://www.valleylab.com/product/vessel_seal/index.html; downloaded Oct. 20, 2005.
Nezhat et al.; U.S. Appl. No. 08/948,282 entitled "Method and systems for organ resection," filed Oct. 9, 1997.
Eder, Joseph C.; U.S. Appl. No. 12/200,798 entitled "Assisted systems and methods for performing transvaginal hysterectomies," filed Aug. 28, 2008.
Koss et al.; U.S. Appl. No. 12/748,229 entitled "Impedance mediated power delivery for electrosurgery," filed Mar. 26, 2010.
Koss et al.; U.S. Appl. No. 12/907,646 entitled "Impedance mediated control of power delivery for electrosurgery," filed Oct. 19, 2010.
Walberg, Erik; U.S. Appl. No. 13/021,633 entitled "Laparoscopic radiofrequency surgical device," filed Feb. 4, 2011.
Kerver et al.; U.S. Appl. No. 13/070,391 entitled "Articulable electrosurgical instrument with a stabilizable articulation actuator," filed Mar. 23, 2011.
Eder et al.; U.S. Appl. No. 13/096,912 entitled "Apparatus for Tissue Cauterization," filed Apr. 28, 2011.
Japanese Office Action mailed Mar. 24, 2015 for Japanese Application No. 2013-529152.

\* cited by examiner

ELECTROSURGICAL TISSUE SEALING AUGMENTED WITH A SEAL-ENHANCING COMPOSITION

CROSS-REFERENCE TO RELATED APPLICATIONS

This application claims priority to U.S. Provisional Patent Application No. 61/384,201 of Van Lue, entitled "Electrosurgical tissue sealing with a seal-enhancing composition", as filed on Sep. 17, 2010.

INCORPORATION BY REFERENCE

All publications and patent applications mentioned in this specification are herein incorporated by reference to the same extent as if each such individual publication or patent application were specifically and individually indicated to be so incorporated by reference.

FIELD OF THE INVENTION

The disclosed technology relates to systems and methods for electrosurgery. More particularly, the technology relates to inclusion of agents that promote tissue sealing when the tissue receives radiofrequency energy from a bipolar electrosurgical device.

BACKGROUND OF THE INVENTION

Bipolar electrosurgical instruments apply radiofrequency energy to a surgical site to cut, ablate, or coagulate tissue. A particular application of these electrosurgical effects is to seal blood vessels or tissue edges. A typical instrument includes an end effector in the form of a pair of opposing jaws, with one or more electrodes on each jaw tip. In an electrosurgical procedure, the electrodes are placed in close proximity to each other as the jaws are closed on a target site such that the path of current between the two electrodes passes through tissue within the target site. The mechanical force exerted by the jaws and the electrical current combine to create the desired surgical effect. By controlling the level of mechanical pressure applied by the jaws, the gap distance between electrodes, and the intensity, frequency, and duration of the electrosurgical energy applied to the tissue, the surgeon can coagulate, cauterize, or seal tissue toward a therapeutic end.

Various approaches have been developed to control the delivery of energy during an electrosurgical procedure, including feedback to the output from a generator delivering energy to the electrodes, such as feedback based on the impedance in target tissue. The goal is to leave a high integrity seal surrounded by healthy tissue by applying no more and no less than the amount of energy required to create the desired effect within the targeted sealing site, while minimizing deleterious effects outside the target locale.

An anatomical variable that poses a challenge to the control and the efficacy of radiofrequency-based sealing relates to variation in the biochemical composition of target tissues. For example, one factor that may affect the success of electrosurgical sealing procedures relates to the relative collagen content of tissues. Tissues with a relatively high collagen content appear to be particularly amenable to effective sealing, while tissues with a relatively low collagen content (such as veins, muscle, kidney, spleen, lung, and liver) are relatively difficult to seal electrosurgically. Devices or methods that enhance the amenability of low collagen tissues to electrosurgical techniques could permit expansion of technology into these organ sites, and allow replacement of conventional methods of sealing, such as the use of staplers and sutures.

SUMMARY OF THE INVENTION

Embodiments of the disclosed technology include systems, devices, and methods for buttressing or bolstering an electrosurgically sealed tissue site. The method may also be understood as one of augmenting, or fortifying an electrosurgically sealed tissue site. Electrosurgical sealing may also be referred to as tissue bonding, annealing, or welding, and may be coupled with or followed by a cutting procedure through the sealed region to separate tissue portions. Embodiments of seal-enhancing compositions, together with tissue sheets at a target site, are processed by a combination of radiofrequency (RF) energy and applied pressure to anneal and form a high integrity sealed site.

In some embodiments of the technology, electrosurgical devices that typically include an end effector, such as jaws or forceps, further include a reservoir that holds a seal-enhancing composition. Embodiments of the device are typically configured to provide or deliver the seal-enhancing composition to a tissue site targeted for electrosurgical sealing. In other embodiments, electrosurgical devices, cooperate with ancillary devices, such as seal-enhancing composition delivery devices, to form a system that provides a seal-enhancing composition to the site targeted for electrosurgical sealing. Embodiments of the technology may be directed toward the sealing of tubular or luminal anatomical structures, such as blood vessels or organs of the gastrointestinal tract. Examples of procedures that may be implemented by embodiments of the disclosed technology thus may include sealing and resection of luminal structures, or anastomoses of luminal structures. Accordingly, in describing the target site, reference will be made to luminal structures, and to their internal and external surfaces and aspects. Embodiments of systems, devices, and methods of the disclosed technology, however, may also be applied to non-luminal anatomical structures, such as sheets or layers of tissue, or to solid organs. Tissue sealing methods applied to luminal organs may be generally considered to be a form of sealing two tissue sheets in that when electrosurgical jaws compress a portion of a luminal structure, the flattened apposed walls form a target tissue site comprising two apposing tissue sheets, albeit joined at their longitudinal edges. Tissue sealing procedures, as performed with embodiments of the disclosed technology, may include the sealing of tissue portions in a side-to-side manner or in an end-to-end manner.

Some embodiments of the technology take the form of an electrosurgical device that includes a set of opposing jaws configured to close on a targeted tissue-sealing site and apply pressure thereto, one or more electrodes associated with each of the jaws, the electrodes disposed on a tissue-facing surface of the jaws. Device embodiments may further include a reservoir configured to hold a tissue seal-enhancing composition within the jaw set, the reservoir in communication with a surface of the tissue-sealing site when the jaws are closed thereon, the electrosurgical device configured to deliver the tissue seal-enhancing composition to the tissue-sealing site during an electrosurgical procedure. Device embodiments are generally configured to be able to deliver sufficient radiofrequency energy to the tissue-sealing site such that the targeted tissue and the tissue seal-enhancing composition that has been delivered to the tissue-sealing site are processed by the energy to form a sealed tissue site.

Some embodiments of the device may further include a handle and an elongated shaft, the set of jaws being disposed at the distal end of the shaft, the shaft being supported at its proximal end by the handle. Some device embodiments may further include a blade and a blade drive member collectively configured to be able to separate tissue at a target site into two portions when the tissue is captured within the set of jaws.

Embodiments of a fully loaded device may include a seal enhancing composition disposed within the reservoir. Some embodiments of the seal-enhancing composition are heat-reformable as a whole, or include components that are heat-reformable. Heat-reformable compositions are typically polymeric and individual molecules, particularly protein molecules, may be cross-linked and/or organized into larger order fibers. On exposure to heat, the component molecules of the seal-enhancing composition melt, disentangle, and liquefy. On cooling, they solidify into a new form with new cross-linking associations, and a new macroscopic solid form. In some aspects, heat may cause a loss or denaturing of native secondary, tertiary, or quaternary levels of structure, and cooling may allow a renaturing or reformation into altered secondary, tertiary, or quaternary levels of structure.

When a seal-enhancing composition is exposed to RF energy in proximity to a target tissue, the seal-enhancing composition may intermingle, intercalate, integrate, coalesce, or adhere to elements of target tissue. The resulting heat-processed mass, derived both from the tissue and the composition, comprises a sealed tissue site. Further, when the seal-enhancing composition includes a protein such as collagen, such collagen molecules within the seal-enhancing composition may form molecular association with collagen molecules of the tissue of the targeted sealing site.

Embodiments of the seal-enhancing composition may include natural products such as collagen or collagen-rich preparations, elastin or elastin-rich preparations, and compositions that include both collagen and elastin. Natural products may be derived from plant or animal sources, such animals including mammals, fish, and birds. Seal-enhancing compositions may also include heat-reformable synthetic compositions such as thermoplastic polymers, or any combination of natural and synthetic heat-reformable products. Seal-enhancing composition embodiments may further include a combination of natural products, such as proteins or carbohydrate compounds, as well as organic polymers, such as polycaprolactone. Seal-enhancing compositions are typically biocompatible, and may be bioabsorbable, bioerodible or biodegradable.

Some embodiments of the seal-enhancing composition may include a sealant or an adhesive. In some embodiments, the sealant or adhesive may be heat-activatable or heat curable, in that the composition remains flowable or non-adherent until it is exposed to heat, whereupon it sets into a form of irreversible stability. In some embodiments, the sealant or adhesive may be moisture or water-activatable or curable, in that the composition remains flowable or non-adherent until it is exposed to moisture, whereupon it sets into a form of irreversible stability. In still other embodiments, the sealant or adhesive includes two or more component compositions that are maintained separately prior to being admixed to form the final sealant or adhesive composition. In some embodiments, the sealant or adhesive includes a cyanoacrylate composition, as for example, compositions that include any one or more of methyl cyanoacrylate, ethyl cyanoacrylate, butyl cyanoacrylate, or 2-octyl cyanoacrylate.

In some embodiments of the technology, the seal-enhancing composition or some portion of it may endure at the sealed tissue site for the lifetime of a patient, or alternatively, the composition may degrade and ultimately disappear, the sealed tissue site eventually assuming characteristics of a natural scar. Further, embodiments of the seal-enhancing composition may include compounds that are not necessarily heat-reformable or heat-curable, but nevertheless act as advantageously in the creation of a sealed tissue site. For example, some components of seal-enhancing composition may act merely as a vehicle for heat-reformable or heat-curable compounds, or otherwise stabilize more active sealing agents or compounds or facilitate their incorporation into a sealed tissue site. Further still, embodiment of the seal-enhancing composition may include bioactive agents that support or accelerate wound healing.

Embodiments of the device may further include a composition delivery mechanism that is adapted to convey or deliver a tissue seal-enhancing composition from the reservoir to the tissue-sealing site. Embodiments of the device are generally directed toward sealing a tissue site that includes either portions of two apposing sheets or layers of tissue, or a flattened portion of a luminal organ or vessel. A luminal structure may also be understood as being two sheets of tissue formed by the action of electrosurgical device jaws being closed thereon. Accordingly, the sealing site has a broadly external surface that includes the combined external surfaces of the two sheets of tissue, an intra-tissue space comprising the whole of the tissue mass between the jaws, and an internal space defined by the facing surfaces of the two sheets of tissue.

In some embodiments of the device, the delivery mechanism is adapted to deliver the tissue seal-enhancing composition to the external surface of the tissue-sealing site. In other embodiments of the device, the delivery mechanism is adapted to deliver the tissue seal-enhancing composition into an internal aspect of a tissue sheet or within the tissue mass grasped by the jaws of the device (i.e., beneath the surface of the tissue, or within the tissue portion) of the tissue-sealing site. In still other embodiments, the delivery mechanism is adapted to deliver the tissue seal-enhancing composition to the internal space between tissue sheets, or within the flattened intraluminal location of the tissue-sealing site.

Embodiments of the delivery mechanism may take various forms, each mechanism providing a communication between the reservoir and the targeted tissue-sealing site. For example, in some embodiments, the delivery mechanism may include a hollow needle. In some embodiments, the delivery mechanism may include an array of seal-enhancing composition ejection tubes. In other embodiments, the delivery mechanism may include a needleless injection mechanism. In still further embodiments, the delivery mechanism may include at least one delivery tube longitudinally disposed on a tissue facing surface on at least one of the two jaws, the at least one tube comprising a plurality of holes that allow egress of a seal-enhancing composition. Any of these embodiments may further include a heating element configured to warm the seal-enhancing composition prior to delivery.

Some embodiments of the technology take the form of an electrosurgical tissue-sealing system that includes two devices: an electrosurgical device and a seal-enhancing composition delivery device. More particularly, the electrosurgical device typically includes a set of opposing jaws configured to close on opposing sides of a tissue-sealing site and one or more electrodes associated with each of the jaws, the electrodes disposed on a tissue-facing surface of the jaws and configured to deliver RF energy to the tissue-sealing site.

As summarized above, embodiments of the device are generally directed toward sealing a tissue site that includes either two apposing sheets of tissue or a luminal structure that is substantially formed into two sheets when being compressed by the closing of the jaws of an electrosurgical device. Thus, the sealing site has an external surface that includes the combined external surfaces of the two sheets of tissue and it has an internal space defined by the facing surfaces of the two sheets of tissue. Per this embodiment of a method, the seal-enhancing composition delivery device is configured to be positionable such that a seal-enhancing composition may be delivered to a location positioned between the opposing jaws when they are closed around the tissue-sealing site. The electrosurgical device of the system is generally configured to be able to deliver sufficient radiofrequency energy to the tissue-sealing site such that the targeted tissue and the tissue seal-enhancing composition are processed to form a sealed tissue site.

In these system embodiments, the seal-enhancing composition delivery device typically includes a reservoir for holding a seal-enhancing composition. A fully loaded seal-enhancing composition delivery device embodiment may further include an embodiment of a seal-enhancing composition disposed within the reservoir.

In some particular embodiments, the composition delivery device of a two-device system is configured to be positionable between the jaws and the external surface of the tissue-sealing site when the jaws are closed around the tissue-sealing site. In some embodiments of this two-device system, the seal-enhancing composition delivery device includes a sheath adapted to fit around a tip of at least one of the opposing jaws. In other embodiments, the seal-enhancing composition delivery device or system may include two sheaths, each sheath being adapted to fit around a tip of one the opposing jaws. In other embodiments, the seal-enhancing composition delivery device takes the form of a wrapped element that is configured or adapted to be positionable at least partially around the luminal tissue-sealing site, interposable between the jaws and the tissue-sealing site.

In still further embodiments of a two-device system, particularly in embodiments directed to an application wherein the tissue-sealing site is located on a luminal organ, the seal-enhancing composition delivery device may include a catheter positionable within a luminal organ. In related embodiments of a two-device system, the seal-enhancing composition delivery device is configured to be positionable between the jaws, when the jaws are closed around the tissue-sealing site, and the internal space between the two sheets of the tissue-sealing site.

Embodiments of the technology also include various methods of electrosurgical tissue sealing that include bolstering or buttressing the tissue seal with a seal-enhancing composition; the seal-enhancing composition, along with the target tissue, is processed by pressure and exposure to RF energy to produce sites of sealed tissue. In some embodiments of these methods, the seal-enhancing composition is provided by a delivery mechanism residing within an electrosurgical device, and in other method embodiments, the composition is delivered by a vehicle or device separate from the electrosurgical device. Embodiments of the method may deliver the seal-enhancing composition variously to outer aspects of a seal tissue site, to sites or to space within tissue, or formed within tissue, and/or into an intra-luminal location proximate the tissue site to be sealed.

Thus, some embodiments of an electrosurgical sealing method include providing a seal-enhancing composition to a site targeted for electrosurgical tissue sealing, delivering radiofrequency energy from an electrosurgical device to the targeted tissue-sealing site, and forming a region of sealed tissue at the targeted tissue-sealing site through the processing effects of radiofrequency energy on both the targeted tissue and on the delivered seal-enhancing composition.

These method embodiments may further include cutting through a region of the sealed tissue to separate tissue into two segments. The ultimate disposition of these two tissue segments varies according to particulars of the procedure. In some cases, both separated tissue portions remain in the body, as for example in a dissecting procedure, where tissue is being cleared to provide surgical access to a site of interest. In other cases, one tissue portion remains in the body and is functional within the patient, and the other tissue portion is discarded after being separated, or is destined to atrophy within the patient.

These method embodiments may further include holding or storing the seal-enhancing composition in a reservoir within the electrosurgical device prior to providing the composition to the sealing site. These method embodiments may further include holding the seal-enhancing composition in a reservoir within a device other than electrosurgical device, prior to providing the composition to the sealing site.

Some embodiments of a method of electrosurgical tissue sealing include storing a seal-enhancing composition in a reservoir within an electrosurgical device and delivering the seal-enhancing composition to a tissue site targeted for electrosurgical sealing. As summarized above, embodiments of the method are generally directed toward sealing a tissue site that includes either two apposing sheets of tissue or a luminal structure that is substantially formed into two sheets when being compressed by the closing of the jaws of an electrosurgical device. Embodiments of the method further include delivering radiofrequency energy from the jaws of the electrosurgical device to the targeted tissue-sealing site, and consequently forming a region of sealed tissue at the targeted tissue-sealing site through a combination of effects of radiofrequency energy on both the targeted tissue and on the delivered seal-enhancing composition.

In another aspect, the technology provides a method for delivering a seal-enhancing composition from an electrosurgical device to a tissue site targeted for electrosurgical sealing, the seal-enhancing composition comprising a heat reformable protein and delivering radiofrequency energy from the jaws of the electrosurgical device to the targeted tissue-sealing site. Finally, the method may include forming a region of sealed tissue at the targeted tissue-sealing site through radiofrequency energy induced heat effects on the targeted tissue and on the seal-enhancing composition at the targeted tissue site.

In an aspect of the method that may occur prior to delivering the seal enhancing composition and prior to delivering radiofrequency energy, the method may include compressing the tissue site targeted for electrosurgical sealing with the jaws of an electrosurgical instrument. In an aspect of the method that may occur after forming a region of sealed tissue, the method may further include cutting through the region of sealed tissue to separate the sealed tissue into two portions. Cutting occurs through the operation of a blade driven by a blade-driving member housed within embodiments of the electrosurgical device.

In some embodiments of the method, delivering the seal-enhancing composition includes delivering the composition to an external surface or surfaces of the tissue-sealing site. In other embodiments of the method, delivering the seal-enhancing composition includes delivering the composition into an internal aspect of either or both tissue sheets associated with the tissue-sealing site. In still other embodiments of the method, wherein delivering the seal-enhancing composition comprises delivering the composition to the internal space between tissue sheets or within the lumen of a tissue-sealing site. A combination of the foregoing methods may also be employed.

With more particular regard to a mechanism for delivery, in various embodiments of the method, delivering the seal-enhancing composition may include any of delivering the composition through a hollow needle, delivering the composition through an array of ejection tubes. In still other embodiments of the method, or delivering the composition through a needleless injection mechanism.

Some embodiments of the disclosed method of electrosurgical tissue sealing include the use of a two-device system, as described above, with an electrosurgical device and a sealing composition delivery device. Thus, these embodiments include storing a seal-enhancing composition in a reservoir within seal-enhancing composition delivery device, and delivering the seal-enhancing composition to a tissue site targeted for electrosurgical sealing. The tissue-sealing site includes either two sheets of tissue or a luminal structure substantially formed into two sheets of tissue by the jaws being closed thereon. Thus, the sealing site has an external surface comprising the combined external surfaces of the two sheets of tissue, and an internal space defined by the facing surfaces of the two sheets of tissue. The method further includes delivering radiofrequency energy from the jaws of an electrosurgical device to the targeted tissue-sealing site; and consequently forming a region of sealed tissue at the targeted tissue-sealing site through a combination of effects of radiofrequency energy on both the targeted tissue and on the delivered seal-enhancing composition.

In one aspect of this embodiment of a method, delivering the seal-enhancing composition to the targeted tissue site may include delivering the composition to the external surface of the tissue-sealing site.

In another aspect of this embodiment of a method, delivering the seal-enhancing composition to the targeted tissue site may include delivering the composition to an internal aspect of either tissue sheet of the tissue-sealing site.

Embodiments of the above-summarized technology may include methods wherein aspects or features of any of the method embodiments are combined with those of any other method embodiment.

BRIEF DESCRIPTION OF THE DRAWINGS

FIG. 1A shows the tips of a pair of jaws in an open position, about to close around a targeted sealing site on an intact blood vessel.

FIG. 1B shows the jaws having closed down on the targeted sealing site, creating a closed vessel region.

FIG. 1C shows the movement of sealing composition out of the reservoirs, and into the sealing site of closed vessel region.

FIG. 1D shows reservoirs now empty, the seal-enhancing composition having been transferred onto or within the tissue of the targeted sealing site enclosed within the jaws, the targeted sealing site now being in an impregnated state, and the jaws of the electrosurgical device in the process of delivering energy to the targeted sealing site.

FIG. 1E shows the targeted sealing site, having been exposed to an appropriate amount of RF energy, now in a processed state, a high integrity seal having been formed from the RF energy processing of native tissue in combination with the seal-enhancing composition.

FIG. 1F shows a blade disposed within the jaws in the process of cutting or dissecting a line through the center of the processed tissue.

FIG. 1G shows the jaws having opened, and the sealing site now separated into two newly sealed regions.

FIG. 2A shows the tips of a pair of jaws in an open position, about to close around a targeted sealing site on an intact blood vessel; a seal enhancing composition is positioned within the lumen of the vessel.

FIG. 2B shows the jaws having closed down on the targeted sealing site, creating a closed vessel region, with force being exerted on the two tissue sheets and on the seal enhancing composition at the interface between the two sheets.

FIG. 2C shows radiofrequency energy being delivered by electrodes on the jaws, the radiofrequency current passing through tissue and seal enhancing composition at the target site.

FIG. 2D shows the targeted sealing site, having been exposed to an appropriate amount of RF energy, now in a processed state, a high integrity seal having been formed from the RF energy processing of native tissue in combination with the seal-enhancing composition.

FIG. 2E shows a blade disposed within the jaws in the process of cutting or dissecting a line through the center of the processed tissue.

FIG. 2F shows the jaws having opened, and the sealing site now separated into two newly sealed regions.

DETAILED DESCRIPTION OF THE INVENTION

Figure 1A:
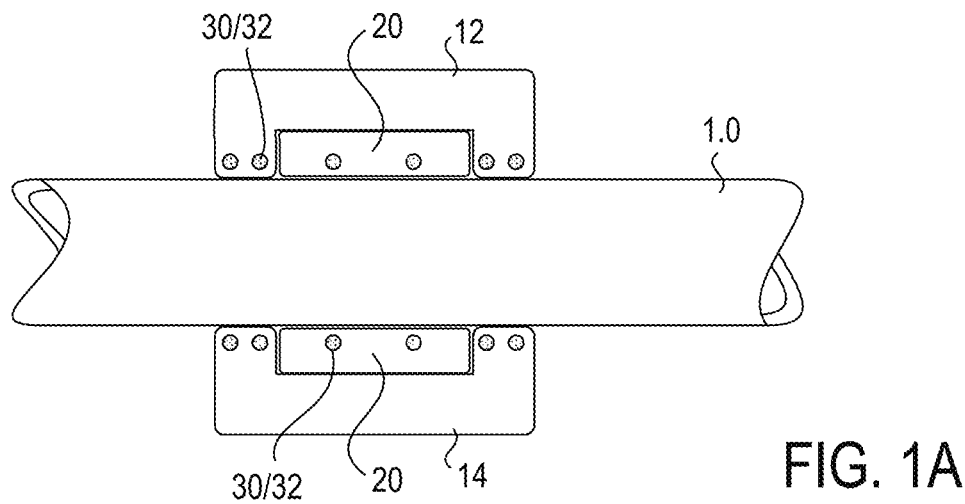
FIGS. 1A-1G show stages in an electrosurgical tissue sealing procedure wherein a seal enhancing composition is applied to an outer surface of a luminal organ tissue site, or impregnated into the tissue.

Embodiments of the technology described herein expand the capabilities of electrosurgical devices that seal tissue to include the ability to associate or integrate a targeted tissue with a seal-enhancing composition that includes heat-reformable components, such as collagen or thermoplastic polymers, or other materials that may be beneficial to the surgical outcome. Associating or integrating a target tissue and a seal-enhancing or seal-fortifying composition may occur in various formats. For example, in the case of a luminal tissue or organ, any of an external (extraluminal) surface or an internal (intraluminal, mucosal) surface may become associated with the seal-enhancing composition; alternatively or, in addition, tissue may become generally impregnated, comingled, infused, or intercalated with a seal-enhancing composition (an intra-tissue site). Upon receiving radiofrequency energy from an electrosurgical device, the seal-enhancing composition is RF energy-transformed to create or contribute to a bolstering or buttressing matrix that enhances efficacy of electrosurgical tissue sealing. The contribution of transformed seal-enhancing composition to a tissue seal can increase the strength and durability of tissue seals generally, and more particularly, can expand the scope of tissues amenable to the use of RF-based tissue sealing. Notably, the provided technology does not include any primary or adjunctive use of staples or sutures to seal tissue.

Electrosurgical tissue sealing, as may be practiced by embodiments of the disclosed technology, generally involves the annealing of two portions, flaps, or sheets of tissue together. These sheets may originate from separate or distant locations within an organ, or they may be originally contiguous, as may occur when portions of a luminal organ or vessel are being sealed together. In other embodiments of the technology, electrosurgical sealing may be advantageously applied to solid organs as well.

Luminal target tissue, particularly tissue associated with larger luminal organs within the gastrointestinal tract, may be considered sheets, or overlapping regions or edges of larger sheets that are annealed together by electrosurgical sealing per embodiments of the technology. In this sense, the outer layer of a luminal tissue site is an anatomically external- or outside-facing surface of a tissue sheet. The inner endothelial layer of a luminal tissue site, in contrast, is an anatomically internal-facing surface of a tissue sheet. Another example of such as internal surface-to-internal surface form of tissue sealing is that of the anastomosis of blood vessels. In the procedural examples described herein, in general, the anatomically internal faces of two tissue sheets are being sealed together, as is the case in currently typical surgical practice. However, embodiments of the method include sealing tissue sheets in other orientations, such as the external face of one sheet and the internal face of another sheet being sealed together, as well as the external facing surfaces of two sheets being sealed against each other. Further, as described below, a tissue sealing composition may be applied between two tissue sheets that are being sealed together, or to one or both of the outer aspects of the tissue sheets as they are positioned for sealing, or to any combination of these alternatives.

In an example of an electrosurgical seal being applied to a blood vessel, a sealing method that applies a seal-enhancing composition to the outer aspect of a vessel encounters the tunica adventitia, which includes relatively tough connective tissue. A sealing composition that is inserted or impregnated into the wall of the vessel encounters the tunica media, which includes a relatively thick layering of connective tissue, elastic tissue, and smooth muscle. A sealing composition that is applied to the luminal surface of a vessel encounters the tunica intima, the thinnest layer of the vessel, which includes endothelial cells underlain by a thin layer of connective tissue.

In an example of an electrosurgical seal being applied to a gastrointestinal lumen, a sealing method that applies a seal-enhancing composition to the outer aspect of an intestinal wall encounters the tunica serosa or adventitia, which comprises relatively tough connective tissue. A sealing composition that is inserted or impregnated into the wall of the intestine encounters the muscular tunic, which includes layers of smooth muscle aligned in various directions. A sealing composition that is applied to the luminal surface of an intestinal wall encounters the mucosal tunic, underlain by a layer of connective tissue and richly invested with a population of secretory cells and glands. Aspects of these various layers vary along the length of the digestive system, from the esophagus, through the stomach and the small and large intestine and rectum. Blood vessels infiltrate all layers of the intestinal wall.

Although description of the technology occurs primarily in the context of luminal organs, other, non-luminal or solid organs may be suitable target tissues for the devices and methods described herein. The technology, may, merely by way of example, be advantageously directed toward therapeutic or surgical procedures of the liver, spleen, pancreas, muscle, lung, fatty tissue, connective tissue, or intestinal membranes, such as the peritoneum, or particular folded portions thereof, such as the omentum.

The present technology provides a method of electrosurgical sealing that includes two particular steps: a first step is to provide a seal-enhancing composition to a tissue site targeted for sealing, a second step is to transform the composition with RF energy with a transient melt or liquefaction and subsequent solidification within the host tissue upon cooling. In a variation of the method, a seal-enhancing composition is melted or partially melted immediately prior to its delivery to the sealing site. Such liquefaction followed by solidification may be understood generally as a manifestation of heat-reformability. More particularly, in the aspects of the technology that include heat-reformability of compositions that include collagen, heat-reformability refers to a dissolution and reformation of strands or fibrils of collagen, and more particularly with regard to chemical bonds between collagen strands. Accordingly, this type of heat-reformation at a molecular level is distinct from a heat reformation that may occur in solid form of a low molecular weight polymer that is melted and then cooled to a new solid form.

In one aspect of the technology, the tissue at the sealing site and the seal-enhancing composition are both substrates for transformation or processing by RF energy delivered by the electrosurgical device. Further, in a sense, the addition of seal-enhancing composition to an RF target site may be understood as a doping of the site that contributes either qualitatively or quantitatively to capacity of the site to form a high integrity seal. The RF-energy product, a region of sealed tissue formed by the technology described herein, has a composition that may include both tissue-derived elements and the transformed seal-enhancing composition. These two component portions of a sealed tissue mass may be intermingled at a microscopic level, or they may form distinct regions, swirls, or layers.

Although embodiments of the seal-enhancing composition may include synthetic polymers, a sealed tissue site per embodiments of the disclosed technology, has features that are associated with the proteinaceous character of the seal-enhancing composition. As is known in the art, some types of tissue are quite amenable to conventional methods of electrosurgical tissue sealing that do not include augmentation with a seal-enhancing composition, while other sites are problematic, and have a mixed record of success. Seal-enhancing compositions, per embodiments of the technology, are particularly advantageous when a targeted sealing site is considered to be a suboptimal candidate for conventional electrosurgical sealing. Tissue seal-enhancing compositions that would rely or substantially rely on relatively low molecular weight polymers or sealants can be anticipated to have a hermetic character, in accordance with the nature of chemical sealants. In contrast, tissue sites that are sealed per embodiments of the provided technology are anticipated to have a character that is not fundamentally or qualitatively different with regard to its porosity or flexibility than that of a conventional and successful electrosurgical seal.

A schematic and more detailed view of an embodiment of the electrosurgical method is provided by FIGS. 1A-1G, wherein a seal enhancing composition is applied to an outer surface of a luminal organ tissue site, or impregnated into the tissue. More specifically, this procedural example represents a luminal site being flattened into a form that can be understood as two sheets being pressed together, the anatomically internal-facing surfaces of each sheet immediately facing each other. Further, in this example, a seal enhancing composition is being applied to both outer surfaces of the two-sheet target site; the composition may remain external to the tissue layer proper, or it may penetrate into the tissue of each sheet.

FIGS. 1A-1G provide an example of an electrosurgical sealing procedure being applied to a blood vessel. These diagrams show a side cross sectional view of the blood vessel being sealed by the tips of electrosurgical jaws; the tips of the jaws are seen in a facing cross sectional view. The targeted sealing site 1 is shown in a series of stages (1.0-1.4) that progress from a preoperative state to a post-operative state, as summarized in Table 1. These stages in tissue processing are described for the purpose of conveying an understanding of tissue processing as it may be performed by embodiments of the provided technology.

The targeted sealing site Stage 0 (1.0) is the site in its native state, prior to any procedural steps. Sealing Site Stage 1 (1.1) is the site in a collapsed or compressed state, being compressed by electrosurgical jaws. Targeted sealing site Stage 2 (1.2) is the site at the stage it is when impregnated or covered with a seal-enhancing composition. In some embodiments stage 1 (compression) and stage 2 (exposure to a seal enhancing composition are effectively combined or achieved simultaneously. Targeted sealing site Stage 3 (1.3) is the site (including both the targeted tissue and the seal-enhancing composition) in transition as it is being driven from its native state to a processed state by delivered RF energy. Targeted sealing site Stage 4 (1.4) is the sealing site, now sealed, the tissue and the seal-enhancing composition having been processed by exposure to RF energy. Sealing Site Stage 5 (1.5) is the completed state of the seal, a blade having separated the processed tissue into two sealed portions.

TABLE 1

Stages of Tissue Processing at a Sealing Site Over the Course of an Electrosurgical Sealing Procedure

| Sealing Stage of Targeted Site | Description of Tissue at the Sealing Site |
|---|---|
| Stage 1.0 | Site in its native or preoperative state, prior to any procedural steps |
| Stage 1.1 | Site in a collapsed or compressed state, being compressed by electro-surgical jaws |
| Stage 1.2 | Site when impregnated, covered, contacted, or otherwise exposed to a seal-enhancing composition in its delivery state, prior to RF exposure |
| Stage 1.3 | Site (including both the tissue and the seal-enhancing composition) in transition as being driven by RF energy from a collective native state to a processed state |
| Stage 1.4 | Site, now sealed, the tissue and the seal-enhancing composition having been processed by exposure to RF energy |
| Stage 1.5 | Site in its completed state, sealed, a blade having separated the processed tissue into two sealed portions |

FIG. 1A shows a cross-sectional view of the tips of a pair of jaws an upper jaw 12 and a lower jaw 14 in an open position, about to close around a targeted sealing site 1.0 on an intact blood vessel. The tips of the jaws, seen in a facing cross sectional view, each include an electrode 20 and reservoirs 30 filled with a seal enhancing composition 32. Embodiments of the technology may have reservoirs disposed on both jaw tips, or on just one of the two tips.

Figure 1B:
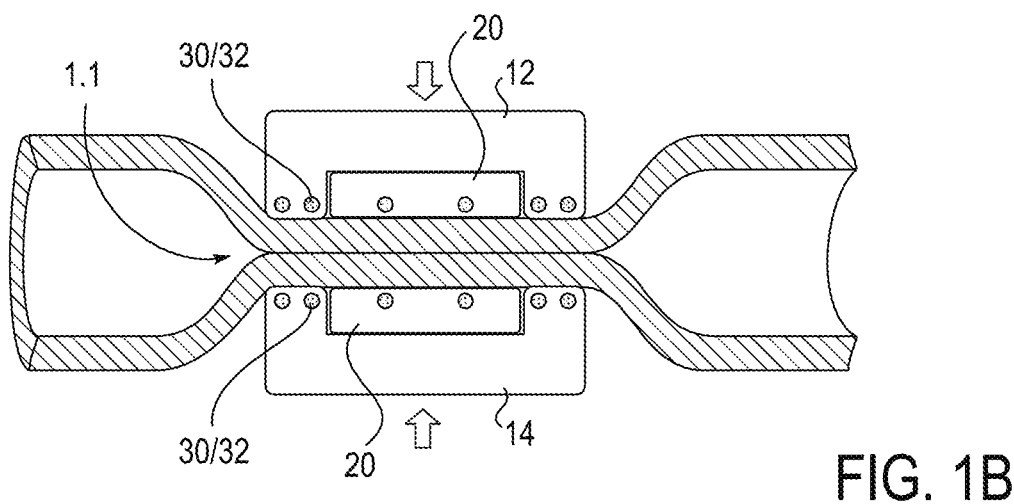

FIG. 1B shows the jaws 12 and 14 having closed down (see directional arrows) on the targeted sealing site 1.1, now shown in a longitudinal cross-sectional view, creating a closed vessel region. Reservoirs 30, filled with a seal-enhancing composition 32, are distributed across the facing surfaces of the jaw tips 20.

Figure 1C:
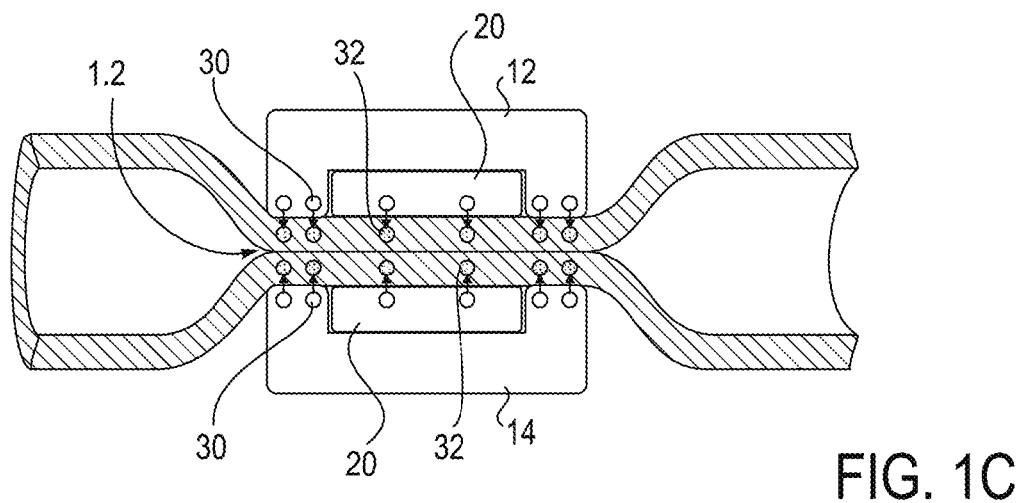

FIG. 1C shows the movement of sealing composition 32 out of the reservoirs 30, and into the sealing site of closed vessel region 1.2. Clamping may occur in two stages; transfer of the seal-enhancing composition may occur during a stage of relatively low force compression, to be followed by a higher pressured compression in preparation for delivery of RF energy, typically delivered in a series of pulses.

Figure 1D:
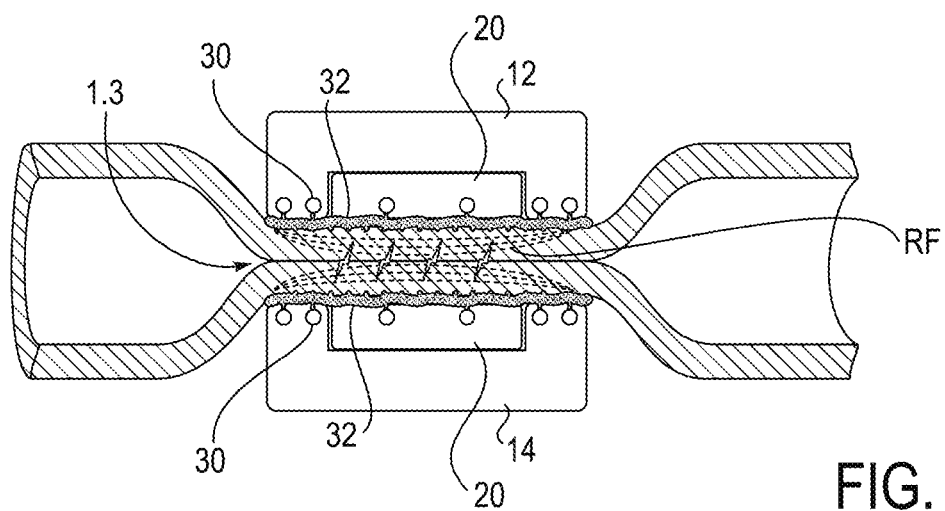

FIG. 1D shows reservoirs 30 now empty, the seal-enhancing composition 32 having been transferred onto or within the tissue of the closed targeted sealing site, the targeted sealing site now being in a coated or impregnated state 1.3. Electrodes 20 on the tips of jaws 12 and 14 are now delivering radiofrequency energy RF to the targeted tissue issue.

The steps shown in FIGS. 1B (clamping), 1C (ejecting seal-enhancing composition into the tissue space), and 1D (delivery of RF energy), may occur as distinct steps, as continuous steps, or as coinciding or overlapping steps. In a particular variation of the method, the seal-enhancing composition 32 may be initially exposed to RF energy even prior to its ejection, in order to facilitate its flowability, transfer, and intercalation into the tissue.

Figure 1E:
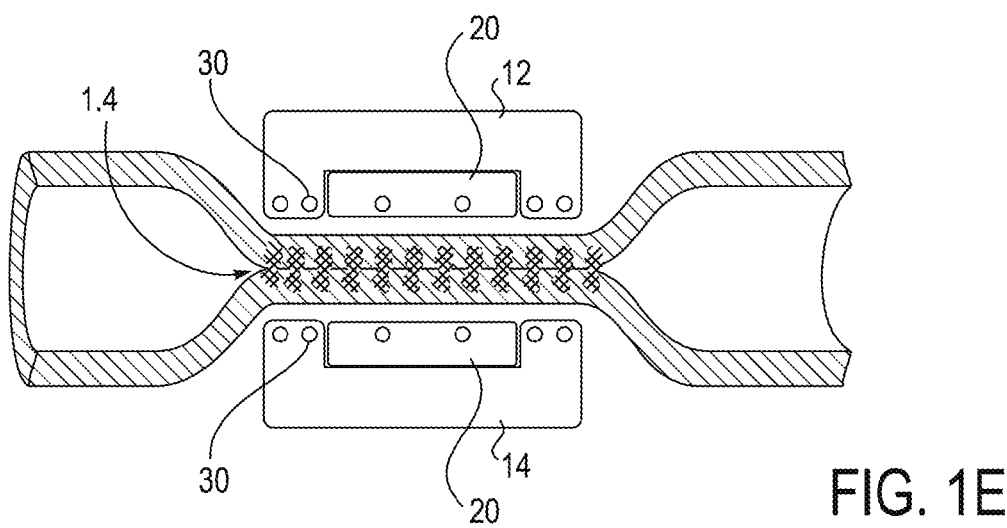

FIG. 1E shows the targeted sealing site, having been exposed to an appropriate amount of RF energy, now in a processed (cross-hatched) state 1.4, a high integrity seal having been formed from the RF energy processing of native tissue in combination with the seal-enhancing composition.

Figure 1F:
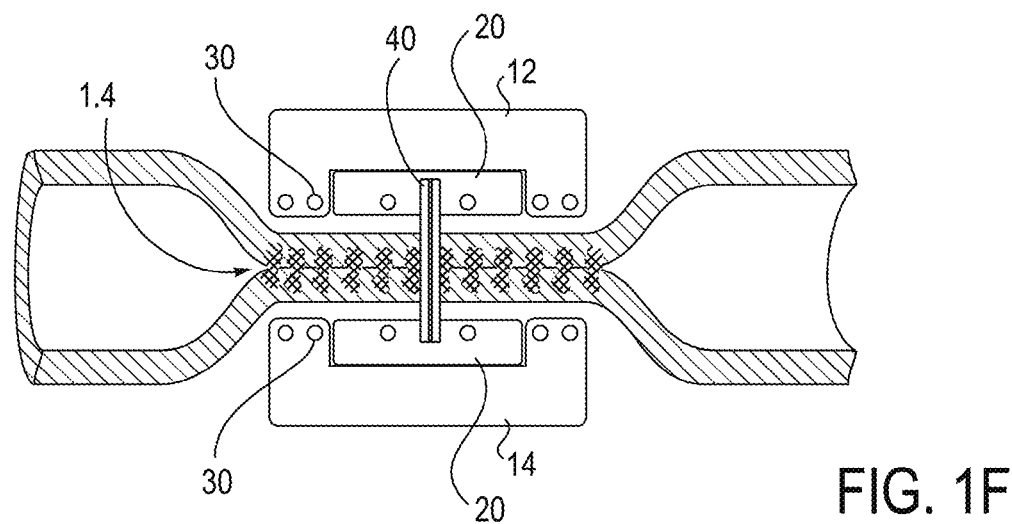

FIG. 1F shows a blade 40 that, until this point, has been disposed proximally within the jaws; the blade now having advanced distally, is in the process of cutting or dissecting a line through the center of the processed tissue at the sealing site 1.4.

Figure 1G:
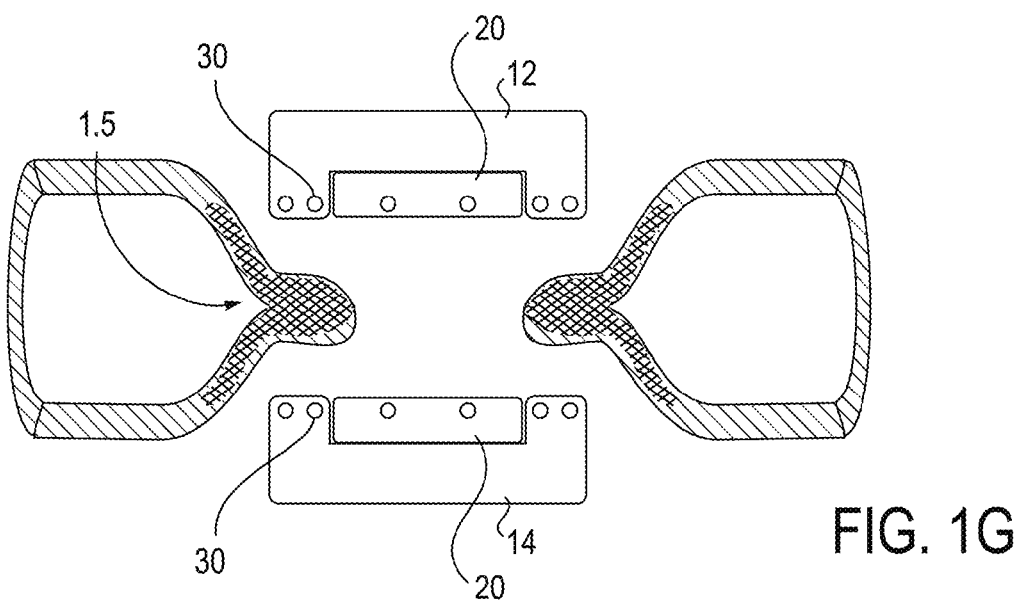

FIG. 1G shows the jaws having opened, and the sealing site now separated into two regions, each of which is a newly sealed site 1.5.

FIGS. 2A-2F depict a variation of the method embodiment described above (relating to FIGS. 1A-1G). In this present variation a seal-enhancing composition may be injected or otherwise inserted into the lumen of an organ or vessel at a target site that is to be sealed, generally prior to a cutting or resection. This procedure contrasts primarily in the location of the seal-enhancing composition with respect to the luminal surfaces or orientation of the target site, and more specifically, with respect to the characteristics of the tissue initially receiving or being contacted by the seal enhancing composition. Thus, FIGS. 2A-2F provide a schematic representation of a seal enhancing composition being applied to an inner surface of a luminal organ tissue sealing site, or being applied or positioned as an interfacing layer between two tissue sheets that are being sealed together.

Figure 2A:
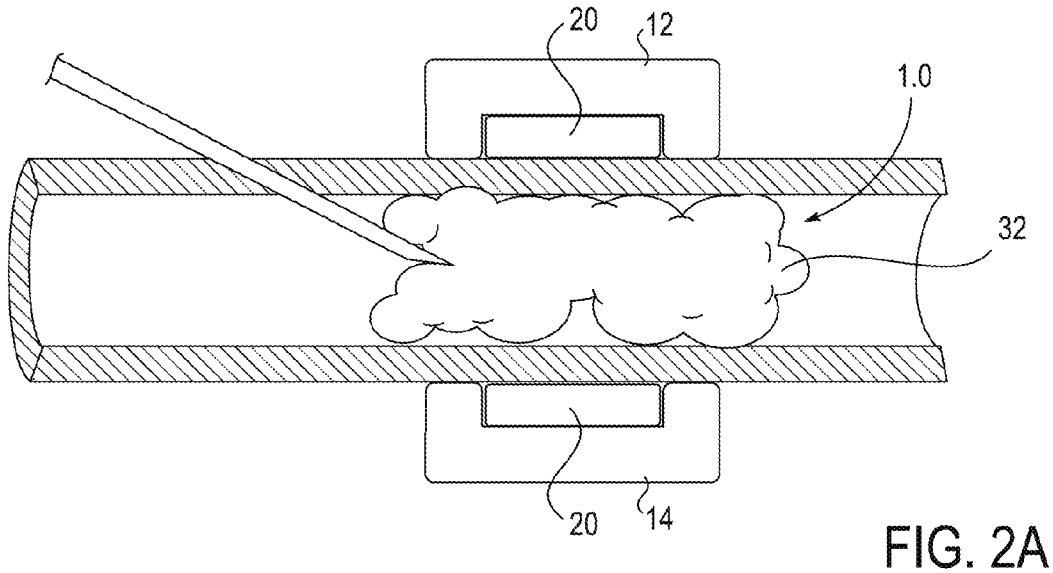
FIGS. 2A-2F show stages in an electrosurgical tissue sealing procedure wherein a seal enhancing composition is applied to an inner surface of a luminal organ tissue site, or impregnated into the tissue.

FIG. 2A shows a facing cross-sectional view of the tips of a pair of electrosurgical jaws, an upper jaw 12 and a lower jaw 14 in an open position, about to close around a targeted sealing site 1.0 on an intact blood vessel, with electrodes 20 in contact with the target tissue. An amount of tissue seal-enhancing composition 32 is present within the lumen. Such composition may be placed there by injection through the luminal wall of the organ being sealed (as shown in FIG. 2A), or it may be placed there by an intravascular route (in the case of a blood vessel) or by passage through the lumen, as per access via a natural orifice of the body (in the case of a gastrointestinal luminal site). For example, a catheter could deliver an amount of flowable seal enhancing composition to a site targeted for sealing, or a catheter could include a solid form of a seal enhancing composition that is placed at the sealing site.

Figure 2B:
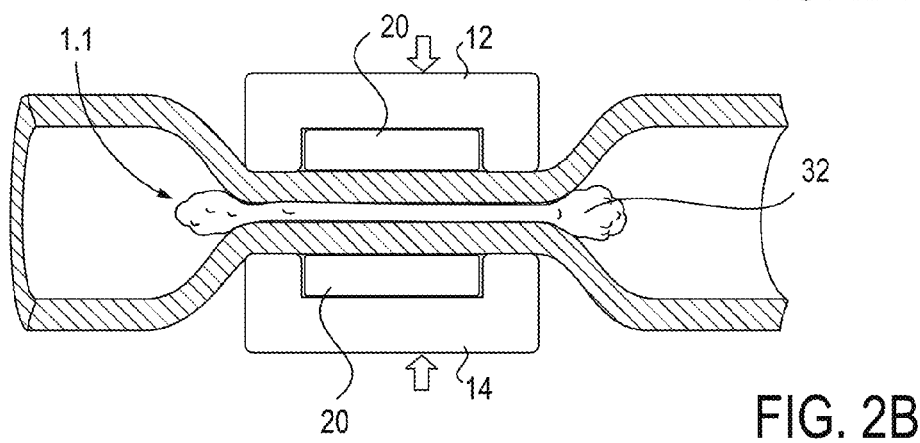

FIG. 2B shows the tips of jaws 12 and 14 having closed down on the targeted sealing site 1.1, creating a closed vessel or organ region. This creates a closed vessel or organ region, with force being exerted on the two tissue sheets and on the seal enhancing composition at the interface between the two sheets.

Figure 2C:
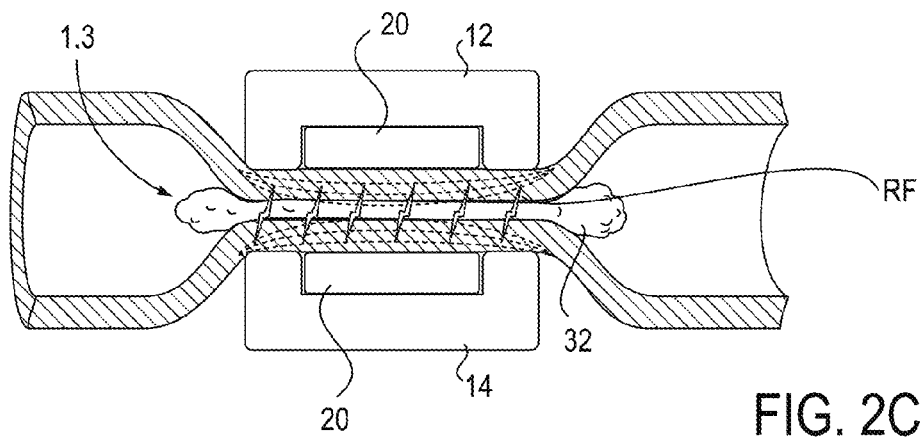

FIG. 2C shows radiofrequency energy being delivered by electrodes on the jaws, the radiofrequency current passing through tissue and seal enhancing composition at the target site. At this stage in the method, the tissue and the seal enhancing composition are at a transitional state 1.3, as they are being processed by exposure to pressure and RF energy.

Figure 2D:
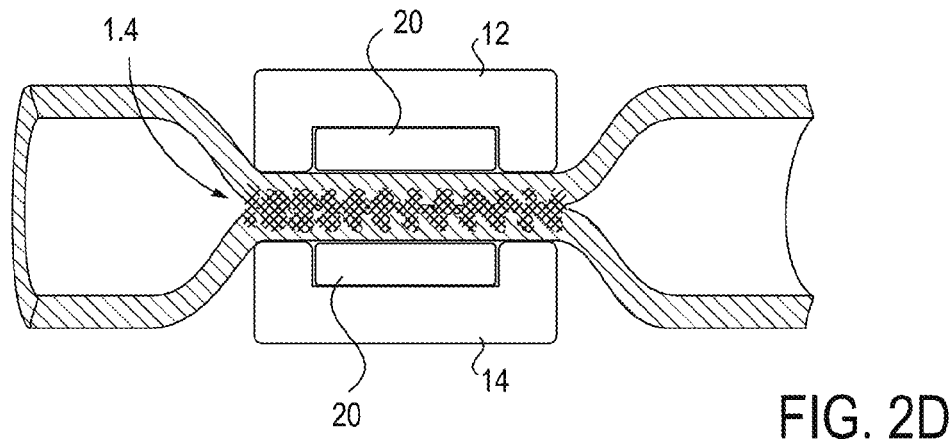

FIG. 2D shows the targeted sealing site, having been exposed to an appropriate amount of RF energy, now in a processed state 1.4 (cross-hatched), a high integrity seal having been formed from the RF energy processing of native tissue in combination with the seal-enhancing composition.

Figure 2E:
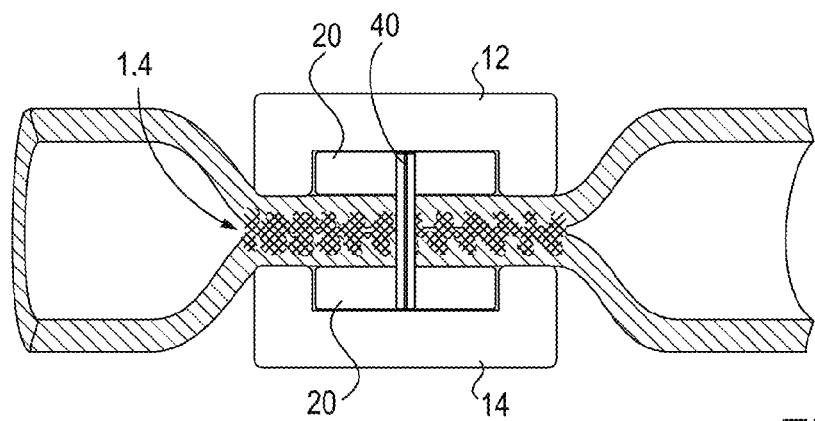

FIG. 2E shows a blade 40 that, until this point, has been disposed proximally within the jaw set; the blade now having advanced distally, is in the process of cutting or dissecting a line through the center of the processed tissue at the sealing site 1.4.

Figure 2F:
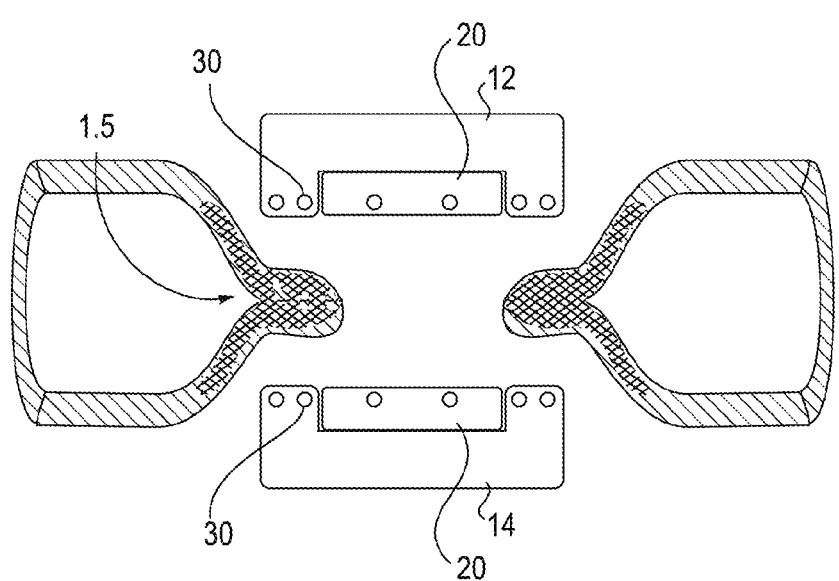

FIG. 2F shows the jaws having opened, and the sealing site now separated into two regions, each of which is a site of newly sealed tissue 1.5.

Embodiments of the provided technology may include a reservoir to hold a seal-enhancing composition, as well as a mechanism to eject or convey the reservoir contents during an electrosurgical procedure. Features and location of the reservoir may vary according to the characteristics of the seal-enhancing composition, as described elsewhere. The location of the reservoir also may vary according the features of the system embodiment. In some embodiments, the system includes an electrosurgical device that itself, provides or delivers the seal-enhancing composition to the targeted site of tissue sealing. In other embodiments of the technology, the system may include two devices, that is, an electrosurgical device with a separate article or device that provides or delivers the seal-enhancing composition.

Embodiments of a reservoir include an overlay of a polymer material, such as a mesh construct, or other material with growth factors, adhesives, anti-adhesives, or any other therapeutically beneficial agent between the RF electrodes of a device and the target tissue. A sleeve or sheath of such material carrying an amount of collagen or other biomaterial suitable for augmenting the radiofrequency-promoted seal may be fitted over end-effector electrosurgical jaws. As one example of a seal-enhancing composition reservoir, some embodiments of the technology include collagen or a collagen-enriched preparation, in the form of pellets, cylinders, or sheets, disposed on the tissue-contacting surface of an electrosurgical jaw in close proximity to the electrode surfaces. These compositional forms may include one or more compounds, and they may include or be formed into layers, regional distributions, or structural features such as pores, that facilitate their delivery to a site targeted for tissue sealing.

Some embodiments of a reservoir may be fitted with a heating element that may be controlled by a mechanism that is separate from the electrical mechanisms controlling the delivery of RF energy. Such heating elements may be advantageous in softening or melting a solid or semi-solid seal-enhancing composition, or they may be advantageous in promoting the flowability of liquid or viscous seal-enhancing compositions.

In some embodiments of the technology, a composition reservoir and a delivery mechanism may be integrated. For example, a seal-enhancing composition may be stored in delivery tube or a hollow needle, which then, upon activation performs a delivery function. In one example, a solid or semi-solid composition form is stored in a tube or needle; upon heating by a heating element, the seal-enhancing composition becomes liquefied, flowable, and deliverable.

Embodiments of the technology vary with regard to the location or placement of the reservoir with respect to the electrosurgical device, and with respect to the internal or external aspect of a targeted sealing site. In some embodiments of the technology, a reservoir is included within or consists of an ancillary unit that is separate from an electrosurgical device itself. These ancillary reservoirs may be placed in proximity to a targeted sealing site either external to a luminal organ or vessel, or within the lumen. In the case where the reservoir is placed external to the lumen, the reservoir is positioned generally between RF-emitting electrodes of the device and the target site. In the case where the reservoir is placed internally, within the lumen of a target site, the reservoir is substantially surrounded by tissue. Further aspects of the reservoir for a seal-enhancing composition are described below in the context of specific embodiments of the technology.

Embodiments of a seal-enhancing composition may include proteins as derived from natural sources or by engineered methods, and they may include synthetic biocompatible polymers. A feature of seal-enhancing composition components that is generally advantageous for use by embodiments of this technology is that of being heat reformable or reformable upon exposure to RF energy. Polymers may be selected for their particular properties that may provide an advantage in this technological application, such as melt temperature, strength, elasticity, or rigidity. Thermoplastic polymers melt under the application of RF energy, and subsequently flow and intercalate into the host tissue of the sealing site. As the melted polymer cools, cross-links develop between and among polymer strands, and the cooling mass as a whole can form a matrix that seals the tissue site. Tissue sealing, in this sense, generally refers to preventing blood or extracellular fluid leakage from the sealed tissue after it has been dissected. With the passage of time, a sealed site may be further infiltrated by biological material originated by the patient; this process may ultimately create even more robust and durable form of tissue seal.

In this medical application, it may be advantageous for polymers to have a relatively low melting point, less than 100 degrees, for example. Monocryl, a product of Ethicon Corporation (poliglecaprone 25™, a segmented block copolymer of epsilon-caprolactone and glycolide, also commonly referred to simply as polycaprolactone or PCL), is an example of a suitable seal-enhancing composition. Monocryl has a melting point of 60 to 70° C., and is an FDA approved biomaterial used in many medical applications. Other polymers that have suitable properties, such as a relatively low melting point, are included as embodiments of the technology.

In some embodiments of the technology, the seal-enhancing composition, in total, may be segregated into component compositions, in separate reservoirs, prior to their delivery to the sealing site. Separate reservoirs may be disposed within an electrosurgical device, in an electrosurgical device and an ancillary device, or within separate compartments within a device ancillary to an electrosurgical device. In some embodiments, one component of a seal-enhancing composition may have a catalytic or curative effect on another component, such that the combination of the two effects the creation of a tissue seal. Further, application or deposition of these separate seal-enhancing components of a seal-enhancing composition may arrive at a luminal sealing site by either an extra-luminal route or by an intra-luminal route.

While a seal-enhancing composition may include a thermoplastic or heat-reformable compound, not all components of the composition need to have such properties. In addition to collagen or elastin, the seal-enhancing composition may include other proteins, such as albumin, or extracellular matrix preparations or constituent proteins such as laminin, fibronectin, or fibrin, by way of example. Suitable biologically derived materials include, by way of example, preparations such as porcine small intestinal submucosa or renal capsule matrix. Polysaccharide components may be included in the composition as well: proteoglycans that associate with proteins, such heparan sulfate, chondroitin sulfate, and keratin sulfate, and non proteoglycan polysaccharides, such as hyaluronic acid.

In some embodiments of the technology, a seal-enhancing composition may include a biocompatible chemical sealant or adhesive. In particular embodiments, embodiments of a seal enhancing composition having a sealant or adhesive may include a cyanoacrylate compound or a compound closely related to cyanoacrylates either physically or functionally. By way of examples, cyanoacrylate-based compositions may include any one or more of methyl cyanoacrylate, ethyl cyanoacrylate, butyl cyanoacrylate, or 2-octyl cyanoacrylate.

In some embodiments, the sealant or adhesive may be heat-curable or moisture-curable, in that the composition remains flowable or non-adherent until it is exposed to the curative conditions, whereupon it takes on an irreversible stability. In the case of moisture-curable sealants or adhesives, the composition remains water-free within a reservoir in the apparatus or in an ancillary composition delivery device until its delivered to a targeted sealing site. Upon delivery to the sealing site, the composition encounters local water and cures into a set form. In the case of heat-curable or heat-activated adhesives or sealants, a composition is delivered to the targeted sealing site, and then subjected to the heat generated in the tissue by conduction of received electrosurgical energy. In response, the flowable composition sets into a fixed form, and contributes to the tissue sealing process. Heat-curable compositions may be formulated as flowable or viscous liquids or gels, or as solid or semi-solid forms that are suspended in a flowable medium. In some embodiments of the technology, wherein a seal enhancing composition may be delivered by an ancillary device (separate from the electrosurgical device), such heat curable compositions may be solid in form.

In still other embodiments, the sealant or adhesive includes two or more component compositions that are maintained separately prior to being admixed to form the final sealant or adhesive composition. In such embodiments, the separate component compositions may be held in separate reservoirs within, external to, or generally in communication with an electrosurgical device. Admixture of component compositions may occur in a common delivery conduit within an electrosurgical device, or alternatively, admixture may occur after release of compositions from an electrosurgical device and delivery of component compositions to the targeted sealing site, whereupon admixture occurs. These compositions may be present in separate physical forms, for example, one component composition may be solid or semi-solid, while the companion composition can be liquid.

A seal-enhancing composition, as provided by embodiments of the technology, may be of any suitable form or formulation, such as solid, a semi-solid, pellets, macro-scale particles, nanoparticles, macro-scale fibers, electrospun fibers, fabrics, a paste, a morcellized biological preparation, a dispersion, a slurry, a liquid, a gel, a spray, or a foam. Fluid vehicles may be aqueous, organic, an emulsion, or an aerosol. Other components may be included in the seal-enhancing composition, such as tissue penetrating agents, detergents, surfactants, or solvents, such as DMSO. Still further, formulation components that serve a stabilizing or preservative function for the composition may be included.

The particular components and their relative concentration in the seal-enhancing composition may be varied to be appropriate for tissues of varied composition; for example, targeted sealing sites in tissues that are low in collagen, or low in water content, may benefit particularly from a collagen-rich seal-enhancing composition. The sealing composition may also be varied to enhance the efficacy of procedures where sealed tissues are subject to particular forms of stress, such as high levels of force, or cycles of force. In other embodiments, the constituents of the sealing promotion composition may be varied so as to be compatible with other materials present at the sealing site, such as suturing or adhesive materials. The disclosed tissue sealing enhancement technology may contribute to sealing success immediately, during the sealing procedure, and it may further promote the long-term integrity of the seal.

Embodiments of seal-enhancing technology described herein are commonly applied to the sealing of luminal tissues sites, such as blood vessels, lymphatic vessels, and gastrointestinal tract sites. However, embodiments of the technology may be usefully applied to electrosurgical procedures directed toward what might be regarded as another end, either immediate or long term, such as to stabilize or to set the stage for healing of an electrosurgical tissue ablation site, a resection site of a solid organ, or a surgical site associated with an amputation or treatment of a traumatic injury. In an ablation procedure, for example, improving the integrity of post-operative tissue, particularly in an interface region between ablated and viable tissue, can contribute to a successful surgical outcome.

While the seal-enhancing technology is described generally in the context of bipolar electrosurgical tissue sealing procedures, embodiments of the method include the application of forms of energy other than bipolar RF energy. For example, energy may be directed to a sealing site by monopolar electrocautery devices. Further, energy may be delivered to a targeted sealing site by devices that deliver microwave energy, laser energy, ultrasound energy, or conductive heat energy by any heating element or medium. Thus, embodiments of the technology, particularly method embodiments, that make use of these alternate forms of energy, are included within the scope of this technology.

In some embodiments of the technology, conventional electrosurgical devices, or such devices with a modest level of adaptation may be used in the application of methods described herein. In these methods, the reservoir of seal-enhancing composition and the manner of providing the seal-enhancing composition to a surgical site are generally separate from the electrosurgical device itself. Examples of tissue sealing systems wherein a reservoir of seal-enhancing composition is provided by a device ancillary to an electrosurgical device, such as a catheter-based system, or an article such as a sheath surrounding one or both of the jaws of an electrosurgical device, or a seal-enhancing wrap system. Examples of some of these embodiments are described further below.

Examples of device and methods that are appropriate for use in conjunction with the seal enhancing composition as provided by an ancillary device or article, per embodiments of the present technology, include the systems, devices, and methods described in the following U.S. issued patents and published patent applications: U.S. Pat. No. 7,862,565 entitled "Method for tissue cauterization" issued on Jan. 4, 2011; U.S. Pat. No. 7,803,156 entitled "Method and apparatus for surgical electrocautery" as issued on Sep. 28, 2010; U.S. Pat. No. 7,794,461 entitled "Method and apparatus for surgical electrocautery" as issued on Sep. 14, 2010; U.S. Pat. No. 8,574,229 entitled "Surgical tool" as issued on Nov. 5, 2013; U.S. Pat. No. 7,942,874 entitled "Apparatus for tissue cauterization" as issued on May 17, 2011; U.S. Pat. No. 8,696,662; entitled "Electrocautery method and apparatus" as issued on Apr. 15, 2014; U.S. application Ser. No. 12/121,734 entitled "Electrocautery method and apparatus" as filed on May 15, 2008 and published on Sep. 11, 2008 as U.S. Publication No. 2008/0221565A1; U.S. application Ser. No. 12/062,516 entitled "Electrocautery method and apparatus" as filed on Apr. 4, 2008 and published on Sep. 18, 2008 as U.S. Publication No. 2008/0228179A1; U.S. application Ser. No. 12/410,322 entitled "Electrocautery method and apparatus" as filed on Mar. 24, 2009 and published on Jul. 16, 2009 as U.S. Publication No. 2009/0182323A1; U.S. Pat. No. 8,728,072 entitled "Electrocautery method and apparatus" as issued on May 20, 2014; U.S. Pat. No. 8,419,727 entitled "Impedance mediated power delivery for electrosurgery" as issued on Apr. 16, 2013, and U.S. Pat. No. 8,827,992 entitled "Impedance mediated control of power delivery for electrosurgery" as issued on Sep. 9, 2014; and U.S. application Ser. No. 13/070,391 entitled "Articulable electrosurgical instrument with a stabilizable articulation actuator", as filed on Mar. 23, 2011 and published on Sep. 22, 2011 as U.S. Publication No. 2011/0230875. These preceding publications are incorporated into this application in their entirety by this reference.

Thus, the technology provides electrosurgical devices that can deliver a seal enhancing composition to a targeted sealing site, and it further provides methods for using minimally adapted electrosurgical devices that can be used in conjunction with a delivery of such a composition by an approach external to the electrosurgical device itself. Examples of systems wherein a reservoir of seal-enhancing composition is provided by a device ancillary to an electrosurgical device include a catheter-based system, a sheath surrounding one or both of the jaws of an electrosurgical device, a seal-enhancing wrap device or composition that is positioned between an electrosurgical energy delivery element and a targeted sealing site, and injection systems. Injection-based delivery systems may make use of hollow needles or needleless mechanisms.

In some embodiments of the technology, an ancillary apparatus is conveyed endoscopically to a site proximate the targeted sealing site, in other embodiments, the ancillary device or reservoir may be brought proximate the sealing site by a surgical approach. In another aspect, ancillary delivery vehicles may perform their delivery in a passive manner, i.e., by way of simple conveyance of composition to the site, as may occur by a catheter. In other embodiments, the ancillary delivery vehicle may operate in a more active manner, as for example, by an injection mechanism.

In other embodiments of the technology, electrosurgical devices incorporate a reservoir and/or mechanisms of delivering a seal-enhancing composition within the device. Embodiments of devices of the technology include those that have any of a hollow needle injection system, a piston-driven delivery system, or a needleless or needle-free injection system. In some of these embodiments, the reservoir may be positioned at various sites within the electrosurgical device that is operably connected to one or more nozzles within the end effector. For example, the reservoir may be located within an end effector, or it may be located proximal to the end effector, such as within the housing of the handle, or within a tubing system that extends proximally to a propulsion mechanism located in the housing of the handle.

Figure 3:
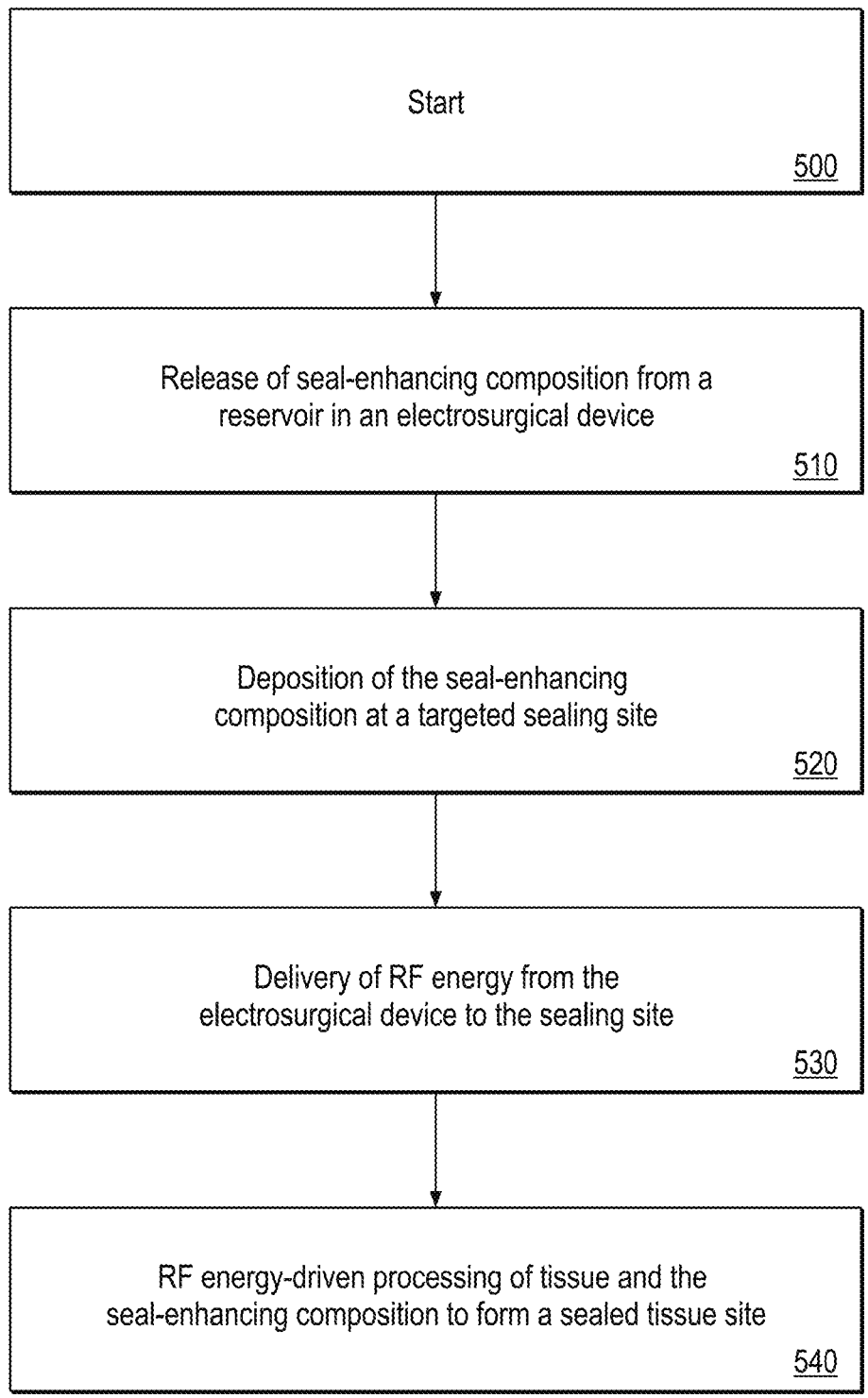
FIG. 3 shows an operational flow diagram of an embodiment of a method of the technology.

FIG. 3 shows an operational flow diagram of an embodiment of a method of the technology. An electrosurgical tissue sealing procedure is initiated at step 500. This step occurs after jaws have been placed in a position where they can grasp a target site for tissue sealing, the jaws have been closed around the site, and appropriate amount of pressure has been applied to the tissue site by the jaws.

An early step 510 in the electrosurgical sealing procedure includes the release of a seal-enhancing composition from a reservoir within or associated with an electrosurgical device. Release of the composition may occur by a mechanical mechanism, as for example by cables that have an actuator associated with the handle of the device, or by electrical or gas-driven powered mechanisms.

Another step 520 involves the delivery of the seal-enhancing composition to the targeted sealing site. As described above, the seal-enhancing composition may be delivered to an external tissue surface associated with the targeted sealing site, it may be delivered internally, within a tissue thickness, and/or, it may be delivered to a site between the faces of adjacent tissue sheets that are to be sealed together. Further, delivery may occur by various mechanisms, for example, delivery may occur through one of more hollow needles, through one or more longitudinally aligned pipes with multiple openings, or by way of an array of delivery tubes through which solid pellets may be expelled.

Step 530 of this example of a procedure includes the delivery of RF energy from electrodes within the jaws of an electrosurgical device to the targeted sealing site.

In step 540 of this example of a procedure, an RF-driven processing of the tissue at the targeted sealing site and the seal-enhancing composition that has been deposited at the sealing site occurs. Steps in this processing have generally been described above in association with Table 1 and in FIGS. 1A-2F.

Examples of device of embodiments of the technology whereby a seal-enhancing composition is held in a reservoir within or associated with the same electrosurgical device that delivers radiofrequency energy to a targeted sealing site are described further below, in association with depictions of FIGS. 4-9B.

Figure 4:
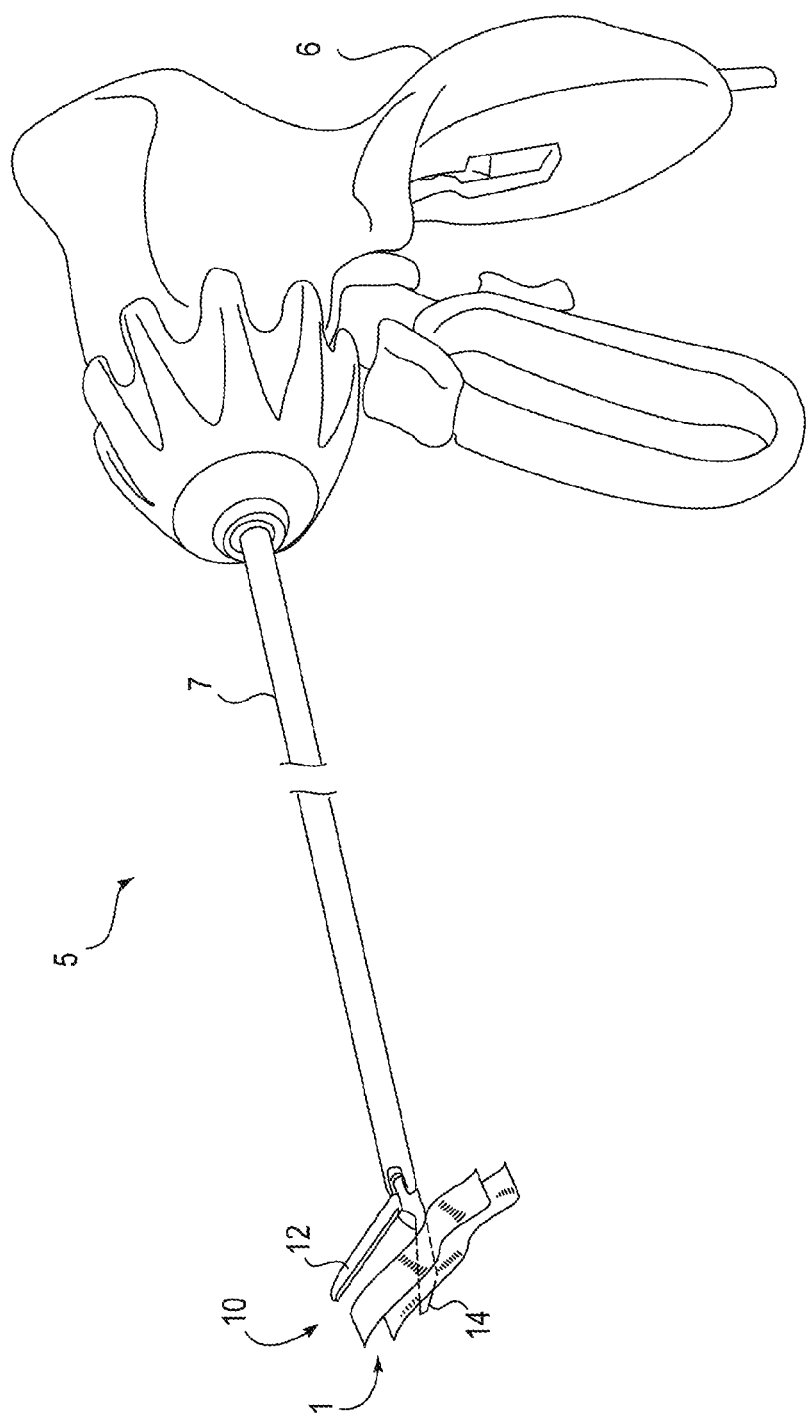
FIG. 4 shows an embodiment of an electrosurgical device with a set of jaws in an open position, about to close on a targeted site for the sealing of two tissue portions.

FIG. 4 provides a perspective view an embodiment of an electrosurgical device 5 having a handle portion 6, and shaft 7 projecting from the handle, and a set of jaws 10 disposed at the distal end of the shaft. Upper jaw 12 and a lower jaw 14 are in an open position with respect to each other. The jaws are positioned such that upon closure, they will close on a targeted site 1 comprising two sheets of tissue. Upon closing of the jaws, compressing the two sheets of tissue, delivering a sealing enhancing composition to the target site, and delivering radiofrequency energy to the target site, the two sheets of tissue will be rendered into a site of sealed tissue.

Figure 5A:
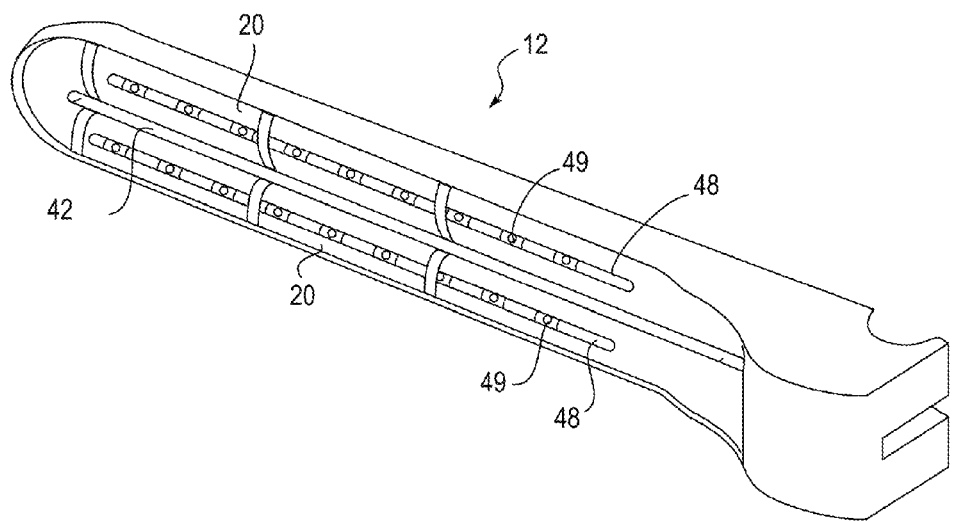
FIG. 5A shows an upper jaw of an embodiment of an electrosurgical device; the tissue facing surface of the jaw includes an electrode and a pair of longitudinally aligned tubes with a plurality of exit holes for the delivery of a seal enhancing composition.
Figure 5B:
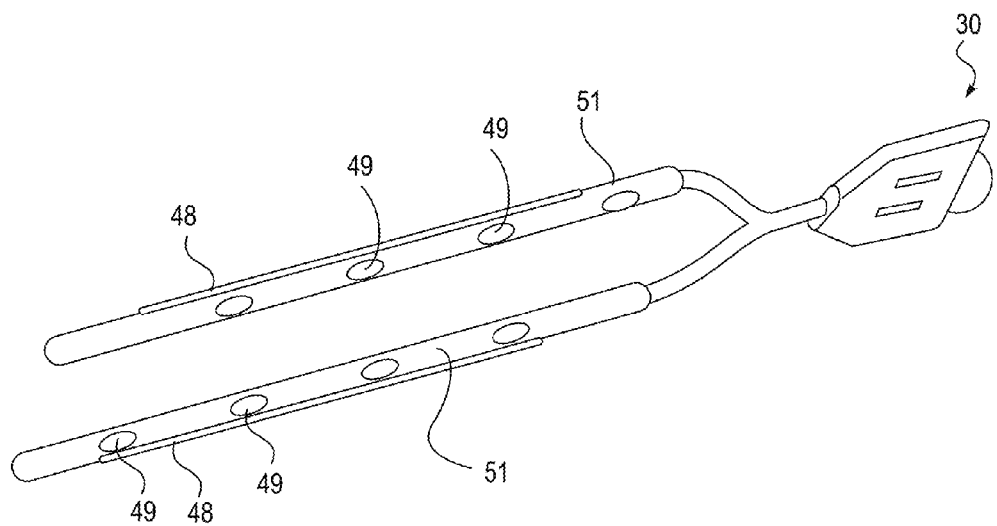
FIG. 5B shows an embodiment of an isolated pair of longitudinally aligned tubes with a plurality of exit holes for the delivery of a seal enhancing composition that are connected to a reservoir, and which further include a heating element.

FIG. 5A shows an upper jaw 12 of an embodiment of an electrosurgical device; the tissue-facing surface of the jaw includes an electrode 20 and a pair of longitudinally aligned composition delivery tubes 48 with a plurality of exit holes 49 for the delivery of a seal enhancing composition. In this embodiment, tubes 48 are disposed on either side a centrally disposed blade track 42. FIG. 5B shows an embodiment of an isolated set of seal-enhancing composition delivery tubes 48. Some tube embodiments may be in communication with a reservoir 30 that holds a volume of sealing composition. Some embodiments of a delivery tube 48 may include a heating element 51, which may also be applied to the surface of reservoir 30. Embodiments of delivery tubes may be adapted for delivery of a solid form seal enhancing composition or a liquid form. In some embodiments, a delivery tube may serve as its own reservoir for a seal-enhancing composition, without the need for a separate reservoir.

A heating element may be advantageous for delivering a seal-enhancing composition that is solid or semi-solid in its native or stored form, heating as delivered by the heating element can melt the composition and facilitate delivery. A heating element may also be advantageous for a seal-enhancing composition that is liquid or viscous in its stored form at room temperature. Such liquid or viscous compositions, warming may increase flowability of the composition, thereby diminishing the possibility of clogging a delivery system, and encouraging the distribution and intercalation of the composition onto or into tissue at the tissue site targeted for sealing.

Figure 6:
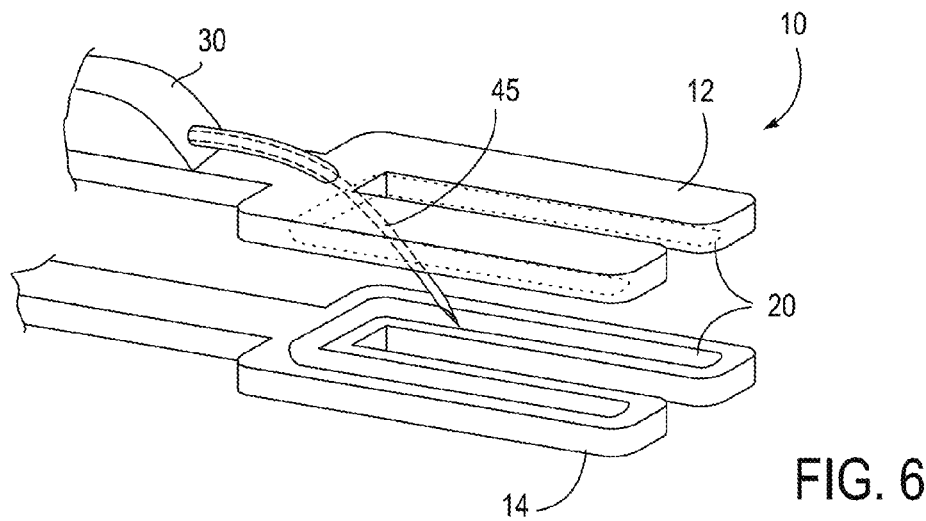
FIG. 6 shows an embodiment of an electrosurgical device with a needle-injection mechanism for delivering a seal enhancing composition.

FIG. 6 shows various components included in a set of electrosurgical jaws that are configured to deliver a seal-enhancing composition to a targeted tissue-sealing site. The jaw set 10 includes an injector in the form of a hollow needle 45 that is operably connected to a reservoir 30 that holds a volume of seal enhancing composition. The needle emerges from one of the two jaws of the jaw set, either an upper or a lower jaw, in proximity to electrodes 20. The needle may have a projecting mechanism that allows it to move from a recessed position to an operating position. The operating position may be controlled such that the seal enhancing composition can be laid out at various depths, such as, for example, at the surface of the target tissue, within the target tissue, or within the lumen of a luminal target tissue site. As described above, an alternative embodiment of an injection delivery system may include a needleless delivery system, with one or more nozzles positioned in proximity to the electrodes, the nozzles fitted proximally with plumbing to a reservoir.

Figure 7:
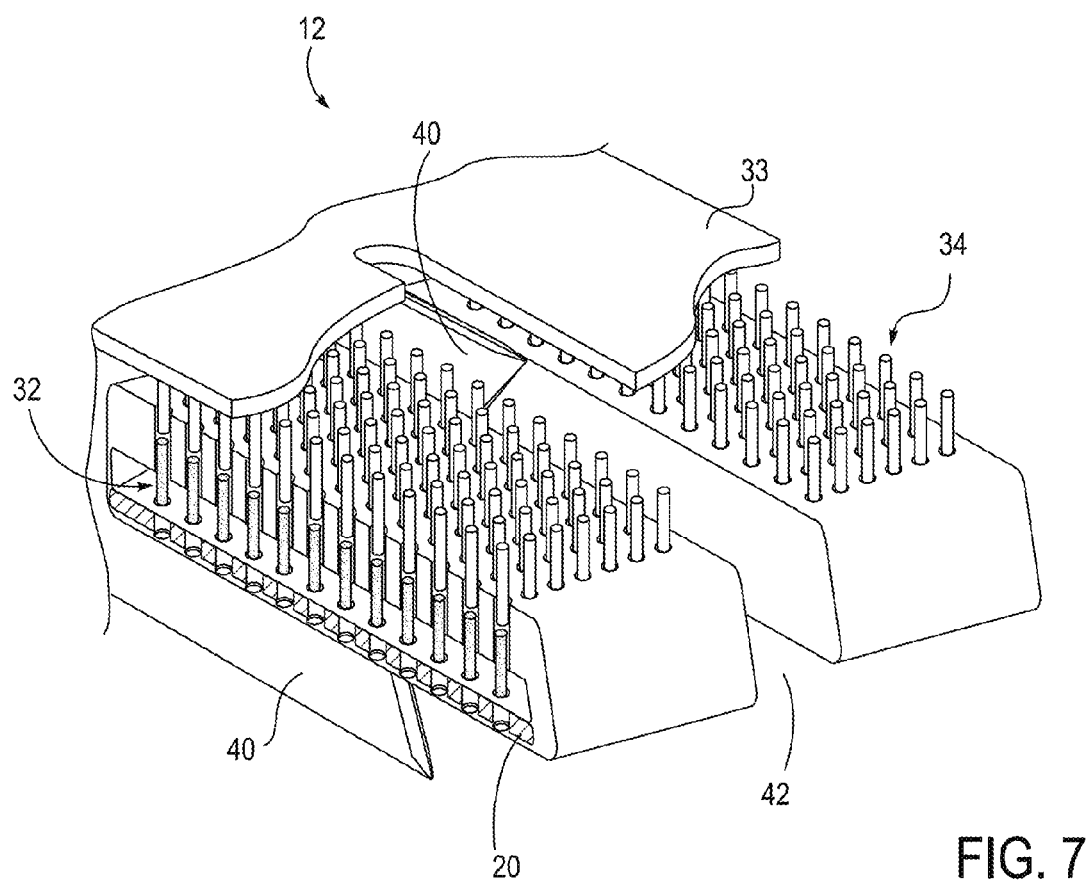
FIG. 7 shows an embodiment of an electrosurgical device with a piston-injection system for delivering a seal enhancing composition.

FIG. 7 shows a portion of the tip of an upper jaw 12 of an embodiment of an electrosurgical device capable of delivering a seal-enhancing composition to a targeted sealing site. Upper jaw tip 12 is fitted with a replaceable modular cartridge comprising an array of multiple pin-shaped pre-loaded sealing composition cylinders 32 and a pressing bar 33 with an array of plungers 34 complementary to the array of composition cylinders. Plungers 34 are configured to be able to press the collagen pellets into the tissue during an electrosurgical procedure generally prior to or during the delivery of RF energy. A transecting blade 40 is disposed within blade slot 42.

When subjected to RF energy delivered by the electrosurgical device, the collagen pellets melt, and become integrated or comingled into the RF-processed tissue within the sealed tissue region. In a procedure that includes the sealing and severing of a blood vessel, for example, collagen, delivered by the jaws and transformed by RF energy, forms a cross linked matrix within the tissue that promotes hemostasis. In a following step of a tissue sealing procedure, blade 40, disposed in slot 42, is advanced through the sealed region between two or more electrode pairs, thereby dissecting the sealed region. The cartridge array 34 containing the seal-enhancing composition 32 may be removed and replaced for further activations of the device in the same patient.

Figure 8A:
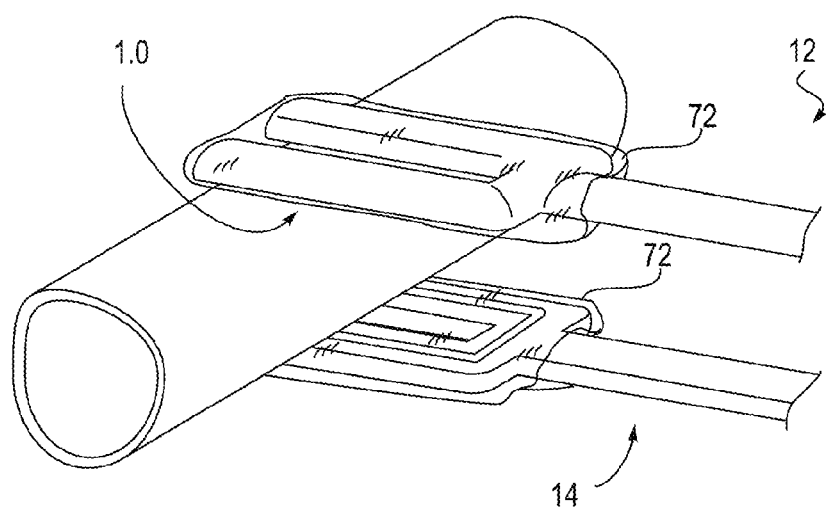
FIG. 8A shows an embodiment of an electrosurgical jaw sheath system for extra-luminal delivery of a seal-enhancing composition positioned to seal a luminal structure.
Figure 8B:
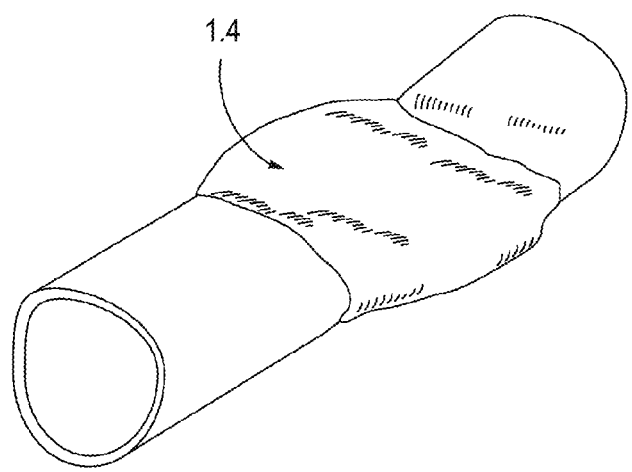
FIG. 8B shows the luminal structure following a sealing procedure per FIG. 8A, but prior to cutting through the sealed tissue.

FIG. 8A shows the tips of upper jaw 12 and lower jaw 14 of an embodiment of an electrosurgical device; each of the tips are at least partially encased with a sheath 72 that includes a reservoir of seal enhancing composition. The tips of the lower and upper jaws are engaging a targeted sealing site 1.0 such as a blood vessel. FIG. 8B shows the targeted sealing site at a stage 1.4, after the electrosurgical sealing device has delivered energy and processed the tissue and the seal enhancing composition into a sealed state. In a step that may follow, a blade can cut the now-sealed tissue site into two separate sealed segments.

Figure 9A:
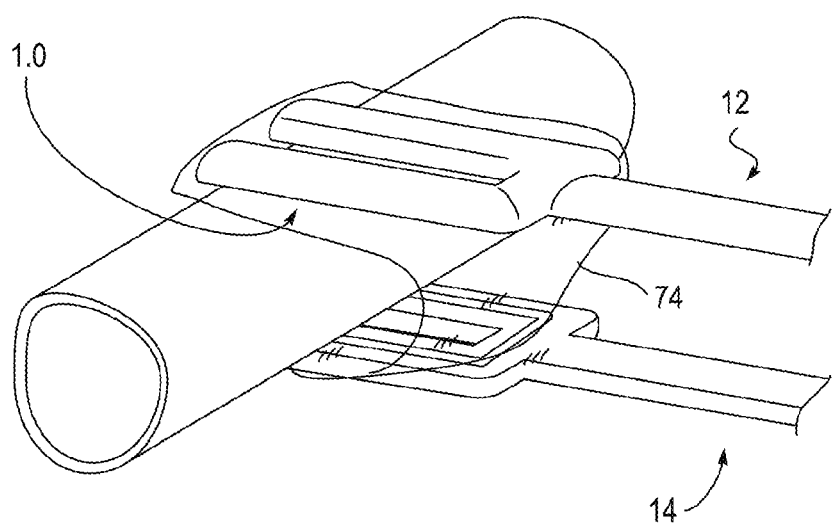
FIG. 9A shows an embodiment of an electrosurgical system for extra-luminal delivery of a wrapped form of a seal-enhancing composition, the jaw tips positioned to seal a luminal structure.
Figure 9B:
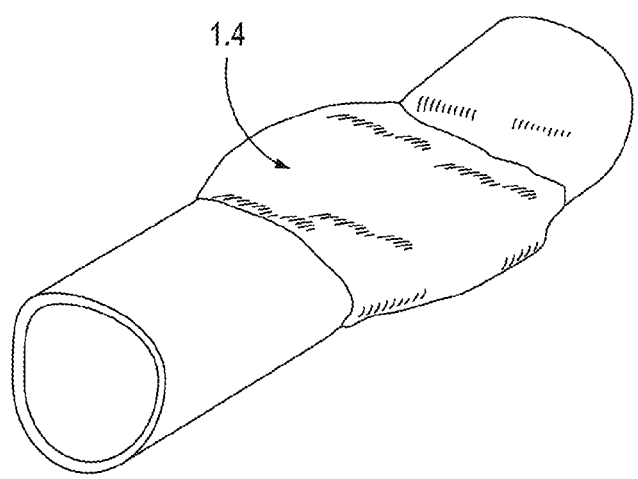
FIG. 9B shows the luminal structure following a sealing procedure per FIG. 9A, but prior to cutting through the sealed tissue.

FIG. 9A shows the tips of upper jaw 12 and lower jaw 14 of an embodiment of an electrosurgical device positioned around a targeted tissue-sealing site 1.0. A sheath 74 that includes a reservoir of seal-enhancing composition is positioned between the jaw tips and the site 1.0 targeted for sealing. FIG. 9B shows the targeted sealing site at a stage 1.4, after the electrosurgical sealing device has delivered energy and processed the tissue and the seal enhancing composition into a sealed state. FIG. 9B shows the sealed site in isolation from the jaws; in a step to follow, the sealed site will be cut by a blade into two separate sealed segments.

Unless defined otherwise, all technical terms used herein have the same meanings as commonly understood by one of ordinary skill in the art of electrosurgery. Specific methods, devices, and materials are described in this application, but any methods and materials similar or equivalent to those described herein can be used in the practice of the present technology. While embodiments of the technology have been described in some detail and by way of illustrations, such illustration is for purposes of clarity of understanding only, and is not intended to be limiting. Various terms have been used in the description to convey an understanding of the technology; it will be understood that the meaning of these various terms extends to common linguistic or grammatical variations or forms thereof. It will also be understood that when terminology referring to devices or equipment, that these terms or names are provided as contemporary examples, and the technology is not limited by such literal scope. Terminology that is introduced at a later date that may be reasonably understood as a derivative of a contemporary term or designating of a hierarchal subset embraced by a contemporary term will be understood as having been described by the now contemporary terminology. Further, while some theoretical considerations have been advanced in furtherance of providing an understanding of the technology, as for example, relating to the dynamics of the response of tissue and of a seal-enhancing composition to absorption of radiofrequency energy, the amended claims are not bound by such theory. Moreover, any one or more features of any embodiment of the technology can be combined with any one or more other features of any other embodiment of the technology, without departing from the scope of the disclosed technology. Still further, it should be understood that the technology is not limited to the embodiments that have been set forth for purposes of exemplification, but is to be defined only by a fair reading of claims appended to the patent application, including the full range of equivalency to which each element thereof is entitled.

The invention claimed is:

1. An electrosurgical device comprising:
a set of opposing jaws configured to be able to close on a targeted tissue-sealing site;
one or more electrodes disposed on a tissue-facing surface of each jaw; and
a reservoir configured to hold a tissue seal-enhancing composition within the jaws, the electrosurgical device configured to deliver the tissue seal-enhancing composition from the reservoir to the tissue-sealing site during an electrosurgical procedure,
wherein the electrosurgical device is configured to deliver sufficient radiofrequency energy to the tissue-sealing site such that tissue and the tissue seal-enhancing composition at the tissue-sealing site are processed to form a sealed tissue site,
the device further comprising a composition delivery mechanism adapted to convey a tissue seal-enhancing composition from the reservoir to the tissue-sealing site, wherein the delivery mechanism comprises an injector in the form of a hollow needle configured to deliver a tissue seal-enhancing composition to the tissue-sealing site, the needle being operably connected to the reservoir, wherein the needle emerges from one of the jaws in proximity to the one or more electrodes,
the reservoir being arranged on top of one of the opposing jaws, wherein each jaw has a U-shaped configuration, the needle being arranged so as to protrude through a first jaw of the opposing jaws and toward a space between the legs of the U-shaped configuration of a second jaw of the opposing jaws, the needle extending completely through a space formed by the U-shaped configuration of the first jaw of the opposing jaws, extending from a top surface of the first jaw to the bottom surface of the first jaw, such that a distal end of the needle is directed at an angle relative to the second jaw of the opposing jaws.

2. The electrosurgical device of claim 1 further comprising a handle and an elongated shaft, the jaws disposed at a distal end of the shaft, the shaft supported at a proximal end by the handle.

3. The electrosurgical device of claim 1, wherein the device further comprises a blade and a blade drive member collectively configured to be able to separate tissue at the tissue-sealing site into two portions when tissue is captured within the jaws.

4. The electrosurgical device of claim 1, wherein the tissue-sealing site comprises two sheets of tissue, the tissue-sealing site thus having an external surface comprising the combined external surfaces of the two sheets of tissue, an intra-tissue space comprising a tissue mass between the jaws, and an internal space defined by facing surfaces of the two sheets of tissue.

5. The electrosurgical device of claim 4, wherein the two sheets of tissue comprise a luminal structure substantially formed into two sheets of tissue by the jaws being closed thereon.

6. The electrosurgical device of claim 4 wherein the delivery mechanism is adapted to deliver a tissue seal-enhancing composition to the external surface of the tissue-sealing site.

7. The electrosurgical device of claim 4 wherein the delivery mechanism is adapted to deliver a tissue seal-enhancing composition into the internal space defined by the facing surfaces of the two sheets of tissue.

8. The electrosurgical device of claim 4 wherein the delivery mechanism is adapted to deliver a tissue seal-enhancing composition to the tissue mass within the tissue-sealing site.

9. The electrosurgical device of claim 1 wherein the needle has a projecting mechanism that allows it to move from a recessed position to an operating position, wherein the operating position is controllable such that a tissue seal-enhancing composition can be laid out at various depths.

10. The electrosurgical device of claim 1 further comprising a tissue seal-enhancing composition within the reservoir.

11. The electrosurgical device of claim 10 wherein the tissue seal-enhancing composition has a heat-reformable property.

12. The electrosurgical device of claim 10 wherein the tissue seal-enhancing composition comprises collagen.

13. The electrosurgical device of claim 10 wherein the tissue seal-enhancing composition comprises elastin.

14. The electrosurgical device of claim 10 wherein the tissue seal-enhancing composition comprises a thermoplastic polymer.

15. The electrosurgical device of claim 10 wherein the tissue seal-enhancing composition comprises a sealant or an adhesive.

16. The electrosurgical device of claim 15 wherein the sealant or adhesive is heat-activatable or heat-curable.

17. The electrosurgical device of claim 15 wherein the sealant or adhesive is moisture-activatable or moisture-curable.

18. The electrosurgical device of claim 15 wherein the sealant or adhesive comprises two or more component compositions that are maintained separately from each other prior to being admixed to form the final sealant or adhesive composition.

19. The electrosurgical device of claim 15 wherein the sealant or adhesive comprises a cyanoacrylate composition.

20. The electrosurgical device of claim 19 wherein cyanoacrylate composition comprises any one or more of methyl cyanoacrylate, ethyl cyanoacrylate, butyl cyanoacrylate, or 2-octyl cyanoacrylate.

21. A method of electrosurgical tissue-sealing, comprising the steps of:
providing an electrosurgical device having a set of opposing jaws configured to be able to close on a targeted tissue-sealing site, one or more electrodes disposed on a tissue-facing surface of each jaw, and a reservoir configured to hold a tissue seal-enhancing composition within the jaws, the electrosurgical device configured to deliver the tissue seal-enhancing composition from the reservoir to the tissue-sealing site during an electrosurgical procedure, the reservoir being arranged on top of one of the opposing jaws, wherein each jaw has a U-shaped configuration, the needle being arranged so as to protrude through a first jaw of the opposing jaws and toward a space between the legs of the U-shaped configuration of a second jaw of the opposing jaws, the needle extending completely through a space formed by the U-shaped configuration of the first jaw of the opposing jaws, extending from a top surface of the first jaw to the bottom surface of the first jaw, such that a distal end of the needle is directed at an angle relative to the second jaw of the opposing jaws;

providing a composition delivery mechanism adapted to convey the tissue seal-enhancing composition from the reservoir to the tissue-sealing site, wherein the delivery mechanism comprises an injector in the form of a hollow needle configured to deliver the tissue seal-enhancing composition to the tissue-sealing site, the needle being operably connected to the reservoir, wherein the needle emerges from one of the jaws in proximity to the one or more electrodes;

holding a seal-enhancing composition in the reservoir within the electrosurgical device;

delivering the seal-enhancing composition to a tissue site targeted for electrosurgical sealing, the tissue-sealing site comprising two sheets of tissue, the tissue-sealing site thus having an external surface comprising the combined external surfaces of the two sheets of tissue, an intra-tissue space comprising a mass of the tissue between the jaws, and an internal space defined by facing surfaces of the two sheets of tissue;

delivering radiofrequency energy from the jaws of the electrosurgical device to the tissue-sealing site; and forming a region of sealed tissue at the tissue-sealing site through a combination of effects of radiofrequency energy on both tissue at the tissue-sealing site and on the delivered seal-enhancing composition.

22. The electrosurgical tissue-sealing method of claim 21 wherein, prior to delivering the seal-enhancing composition and prior to delivering radiofrequency energy, the method comprises the step of compressing the tissue-sealing site.

23. The electrosurgical tissue-sealing method of claim 21 wherein, after forming a region of sealed tissue, the method further comprises the step of cutting through the region of sealed tissue to separate the region of sealed tissue into two portions.

24. The electrosurgical tissue-sealing method of claim 21, wherein the step of delivering the seal-enhancing composition comprises delivering the seal-enhancing composition to the external surface of the tissue-sealing site.

25. The electrosurgical tissue-sealing method of claim 21, wherein the step of delivering the seal-enhancing composition comprises delivering the seal-enhancing composition into an internal aspect of at least one of the two sheets of tissue of the tissue-sealing site.

26. The electrosurgical tissue-sealing method of claim 21, wherein the step of delivering the seal-enhancing composition comprises delivering the seal-enhancing composition to the intra-tissue space within the tissue-sealing site.

27. The electrosurgical tissue-sealing method of claim 21, wherein the step of delivering the seal-enhancing composition comprises delivering the seal-enhancing composition through a hollow needle.

28. A method of electrosurgical tissue-sealing, comprising the steps of:

providing an electrosurgical device having a set of opposing jaws configured to be able to close on a targeted tissue-sealing site, one or more electrodes disposed on a tissue-facing surface of each jaw, and a reservoir configured to hold a tissue seal-enhancing composition within the jaws, the electrosurgical device configured to deliver the tissue seal-enhancing composition from the reservoir to the tissue-sealing site during an electrosurgical procedure, the reservoir being arranged on top of one of the opposing jaws, wherein each jaw has a U-shaped configuration, the needle being arranged so as to protrude through a first jaw of the opposing jaws and toward a space between the legs of the U-shaped configuration of a second jaw of the opposing jaws, the needle extending completely through a space formed by the U-shaped configuration of the first jaw of the opposing jaws, extending from a top surface of the first jaw to the bottom surface of the first jaw, such that a distal end of the needle is directed at an angle relative to the second jaw of the opposing jaws;

providing a composition delivery mechanism adapted to convey the tissue seal-enhancing composition from the reservoir to the tissue-sealing site, wherein the delivery mechanism comprises an injector in the form of a hollow needle configured to deliver the tissue seal-enhancing composition to the tissue-sealing site, the needle being operably connected to the reservoir, wherein the needle emerges from one of the jaws in proximity to the one or more electrodes;

delivering a seal-enhancing composition from the electrosurgical device to a tissue-sealing site targeted for electrosurgical sealing, the seal-enhancing composition comprising a heat reformable protein;

delivering radiofrequency energy from the jaws of the electrosurgical device to the tissue-sealing site; and forming a region of sealed tissue at the tissue-sealing site through radiofrequency energy induced heat effects on tissue of the tissue-sealing site and on the seal-enhancing composition at the tissue-sealing site.

* * * * *